US006225127B1

(12) United States Patent
Thompson et al.

(10) Patent No.: US 6,225,127 B1
(45) Date of Patent: May 1, 2001

(54) ENZYME-BASED FLUORESCENCE BIOSENSOR FOR CHEMICAL ANALYSIS

(75) Inventors: Richard B. Thompson, Baltimore; Marcia W. Patchan, Columbia, both of MD (US); Zhenfang Ge, Burlington, MA (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 09/270,308

(22) Filed: Mar. 15, 1999

Related U.S. Application Data

(62) Division of application No. 08/736,904, filed on Oct. 25, 1996, now Pat. No. 5,952,236.
(60) Provisional application No. 60/005,879, filed on Oct. 26, 1995.
(51) Int. Cl.[7] ..................................................... G01N 33/48
(52) U.S. Cl. ................. 436/76; 436/77; 436/74; 436/73; 436/501; 530/413; 530/412; 530/350
(58) Field of Search ................................ 436/77, 76, 74, 436/73, 501; 530/413, 412, 350

(56) References Cited

U.S. PATENT DOCUMENTS

| | | | | |
|---|---|---|---|---|
| 4,261,968 | * | 4/1981 | Ullman et al. | 424/8 |
| 4,816,419 | * | 3/1989 | Hoffman et al. | 436/546 |
| 5,162,218 | * | 11/1992 | Schultz | 435/188 |
| 5,227,487 | * | 7/1993 | Haughland et al. | 546/15 |
| 5,274,113 | * | 12/1993 | Kang et al. | 436/74 |
| 5,648,270 | * | 7/1997 | Kuhn et al. | 436/74 |
| 5,665,865 | * | 9/1997 | Leorner et al. | 530/387.3 |
| 5,679,548 | * | 10/1997 | Barbas et al. | 435/69.6 |

OTHER PUBLICATIONS

Hackh's Chemical Dictionary, 4th ed. p. 388 Thompson et al, Biosensors & Bioelec. (1996), 11, 557–564.*

* cited by examiner

Primary Examiner—T. Wessendorf

(57) ABSTRACT

This invention generally relates to the detection, determination, and quantitation of certain ions and small molecules involving the quenching of a fluorescent label attached to a macromolecule, often due to fluorescence energy transfer to a colored inhibitor or certain metal ions bound to the macromolecule.

8 Claims, 16 Drawing Sheets

ENZYME-BASED FLUORESCENCE BIOSENSOR FOR CHEMICAL ANALYSIS

This application is a division of U.S. patent application Ser. No. 08/736,904, filed Oct. 25, 1996, now issued U.S. Pat. No. 5,952,236, said application claiming priority to U.S. Provisional Patent Application Ser. No. 60/005,879, filed Oct. 26, 1995.

The development of the present invention was supported by the Office of Naval Research grant number N0001491-1572.

FIELD OF THE INVENTION

The field of this invention generally relates to the detection, determination, and quantitation of certain ions and small molecules. The approach is based upon quenching of a fluorescent label attached to a macromolecule, often due to fluorescence energy transfer to a colored inhibitor or certain metal ions bound to the macromolecule.

BACKGROUND OF THE INVENTION

For scientific, regulatory, or other applications, many persons, institutions, and agencies often require analyses of samples to determine whether such small molecule and ionic analytes are present. Examples of such analyses include the determination of metal ions in sea water to understand the processes of chemical oceanography; determination of toxic materials such as Hg(II), Ni(II), $CN^-$, or $HS^-$ in groundwater or wastewater; detection of the corrosion of metal alloys by the presence of Co(II), Zn(II), or Cu(II) in condensates; or the presence of metals in lubricating oil as an indicator of machinery wear and incipient failure.

Many methods are known in the art for such analyses. For metal ions, such methods include graphite furnace atomic absorption spectrophotometry, inductively coupled plasma atomic emission spectroscopy and mass spectroscopy, various electrochemical means, and fluorescence spectroscopy using metallofluorescent indicators. For common anionic analytes there are fewer techniques available; they include ion chromatography, mass spectrometry, and electrochemical means.

Most of these techniques involve analysis of single or multiple discrete samples in a specialized instrument which may not be close to the sample. This is a particular drawback for analytical tasks that require a continuous or quasicontinuous determination of the analyte with real time readout of the result; require samples to be collected from remote, inaccessible, or hazardous environments; or require such extensive sampling that it is prohibitively costly. For many of these methods a sensor capable of remotely, continuously, and selectively monitoring the analyte of interest in situ is required, and subsequent reporting of the results of the analysis back to the operator in real time.

Improvements have been made in the development of fluorescence-based sensors for a variety of applications (Thompson, R. B. (1991) in *Topics in Fluorescence Spectroscopy*, Vol. 2: *Principles*, Lakowicz, J. R. (Ed.) Plenum Press, NY; Wolfbeis, O. S. (Ed.) (1992) *Fiber Optic Chemical Sensors and Biosensors* Vols. I and II, CRC Press, Boca Raton, Fla.; Lakowicz, J. R., and Thompson, R. B. (Eds.) (1993) *Proc. of the SPIE Conference on Advances in Fluorescence Sensing Technology* Vol. 1885, Society of Photooptical Instrumentation Engineers, Bellingham, Wash.) A central issue in the development of such sensors has been the means of transduction, whereby the presence or relative amount of the chemical analyte is transduced as a change in the fluorescence which may be quantitated. Thus, workers in the field have mainly transduced analyte levels as changes in fluorescence intensity (Thompson (1991); Saari, L. A., and Seitz, W. R. (1982) *Anal. Chem.* 54, 821; Thompson, R. B. and Ligler, F. S. (1991) in *Biosensors with Fiber Optics.*, Wise, D., and Wingard, L. (Eds.) pp. 111–138, Humana Press, Clifton, N.J.), or ratios of fluorescence intensity at two different wavelengths (Tsien, R. Y. (1989) *Ann. Rev. Neurosci.* 12, 227; Opitz, N., and Lubbers, D. W. (1984) *Adv. Exp. Med. Biol.* 180, 757; Thompson, R. B. and Jones, E. R. (1993) *Anal. Chem.* 65, 730–4; and U.S. Pat. No. 5,545,517).

The ratio approach has proven particularly popular because it is robust in avoiding many of the artifacts associated with simple intensity measurements. The major limitation of the ratio approach has been the limited number of ratiometric fluorescent indicators (Haugland, R. P. (1992) *Handbook of Fluorescent Probes and Research Chemicals*, Molecular Probes, Eugene, Oreg.).

Recently, many groups have shown that transducing the level of analyte as a change in fluorescence lifetime is a robust and flexible approach to optical sensing (Demas, J. N., (1994) in *Topics in Fluorescence Spectroscopy*, Vol. 4: *Probe Design and Chemical Sensing*, Lakowicz, J. R. (Ed.) Plenum Press, NY; Lippitsch, M. E., Pusterhofer, J., Leiner, M. J. P. and Wolfbeis, O. S. (1988) *Anal. Chim. Acta* 205, 1–6; Keating, S. M., and Wensel, T. G. (1991) *Biophys. J.* 59, 186–202; Lakowicz, J. R., Szmacinski, H., and Karakelle, M. (1993) *Anal. Chim. Acta* 272, 179–186; Szmacinski, H., and Lakowicz, J. R. (1993) *Anal. Chem.* 65, 1668–74; Lakowicz, J. R. (1992) *Laser Focus World* 28(5) 60–80; Thompson, R. B. and Patchan, M. W. (1993) in *Proc. of the SPIE Conference on Chemical, Biochemical, and Environmental Fiber Optic Sensors V.* Lieberman, R. A. (Ed.) pp. 296–306. Society of Photooptical Instrumentation Engineers, Bellingham, Wash.; Ozinskas, A. J., Malak, H., Joshi, J., Szmacinski, H., Britz, J., Thompson, R. B., Koen, P. A., and Lakowicz, J. R. (1993) *Anal. Biochem.* 213, 264–270). Lifetime-based sensing can exhibit a dynamic range of greater than five orders of magnitude in analyte concentration (Szmacinski, H., and Lakowicz, J. R. (1993) *Anal. Chem.* 65, 1668–74; Thompson, R. B. and Patchan, M. W. (1993) in *Proc. of the SPIE Conference on Chemical, Biochemical, and Environmental Fiber Optic Sensors V.* Lieberman, R. A. (Ed.) pp. 296–306. Society of Photooptical Instrumentation Engineers, Bellingham, Wash.). Lifetime-based sensing has been adapted to and has particular advantages for fiber optic sensors.

The development of fluorescence-based fiber optic biosensors is well documented. In particular, optical designs which optimize fluorescence measurements through optical fiber are described (U.S. Pat. No. 5,141,132), a sensor suited for the determination of anesthetics and other lipid-soluble analytes (U.S. Pat. No. 5,094,819), and an optical design which optimizes the sensitivity of so-called evanescent-wave sensors (U.S. Pat. No. 5,061,897) have been described. The advantages of fiber optic sensors for remote, continuous monitoring of analytes in environments that are hazardous or inaccessible are well known (Thompson, R. B. (1991) in *Topics in Fluorescence Spectroscopy*, Vol. 2: *Principles*, Lakowicz, J. R. (Ed.) Plenum Press, NY; Wolfbeis, O. S. (Ed.) (1992) *Fiber Optic Chemical Sensors and Biosensors* Vols. I and II, CRC Press, Boca Raton, Fla.; Thompson, R. B. and Ligler, F. S. (1991) in *Biosensors with Fiber Optics.* Wise, D., and Wingard, L. (Eds.) pp. 111–138, Humana Press, Clifton, N.J.).

Recently, a fiber optic biosensor for metal ions in aqueous solution that takes advantage of the very selective binding of particular metals by the enzyme carbonic anhydrase II from mammalian erythrocytes has been described. (Thompson, R. B. and Jones, E. R. (1993) *Anal. Chem.* 65, 730–4; Thompson, R. B. and Patchan, M. N. (1993) in *Proc. of the SPIE Conference on Chemical, Biochemical, and Environmental Fiber Optic Sensors V.* Lieberman, R. A. (Ed.) pp. 296–306. Society of Photooptical Instrumentation Engineers, Bellingham, Wash.; and U.S. Pat. No. 5,545, 517). It was shown that metal-dependent binding of a fluorescent aryl sulfonamide inhibitor, dansylamide, could be transduced as a change in the ratio of fluorescence emission intensities at two different wavelengths (450 and 550 nanometers (R. B. Thompson and E. R. Jones, *Anal. Chem.* 65: 730–4 (1993)), or changes in the fractional contributions of two fluorescence lifetimes arising from the bound and free forms of the dansylamide (see FIG. 1) (R. B. Thompson and M. W. Patchan, *J. Fluorescence* 5:123–30 (1995)). These fluorescence observables are related to the fraction of enzyme with dansylamide bound to it, which is equal to the fraction of enzyme with Zn(II) in its active site and simply related to the concentration of the analyte Zn(II) by the law of mass action. These methods demonstrate rapid determination of Zn(II) at nanomolar levels in aqueous solutions.

However, dansylamide has some properties which are suboptimal. It must be excited by ultraviolet light at approximately 330 nanometers, a regime at which typical optical fiber exhibits high attenuation and background fluorescence, and for which available light sources are relatively inconvenient and expensive. While it is desirable to find a fluorescent inhibitor akin to dansylamide but excitable in the visible or near infrared, searches of the extensive literature of arylsulfonamide inhibitors of mammalian carbonic anhydrases failed to elicit a compound with the desired properties (Bar, D. (1963) *Act. Pharm.* 15, 1–44). Colored inhibitors such as azosulfamide are known in the art (Krebs *Biochem. J.*, 43:525–528 (1948)). However, their use as an additional ligand on an active site metal ion or ligand to quench by energy transfer is first demonstrated by the present invention. While this inhibitor, azosulfamide, does not fluoresce significantly itself, the present invention demonstrates transduction of zinc-dependent binding to the enzyme as a change in fluorescence lifetime using the technique of energy transfer.

Ullman (U.S. Pat. No 4,261,968) teaches a fluorescence immunoassay wherein a fluorescent-labeled antibody is brought in contact with a sample containing antigen (the analyte) and a quencher-labeled antigen; the unlabeled antigen (of unknown concentration) and labeled antigen (of known concentration) compete for the antibody recognition site. The fluorescence emission of the label is quenched to a degree inversely proportional to the unlabeled antigen concentration, and thus serves as a measure thereof. Ullman does not teach analysis of metal ions or small anions, or the use of a ligand whose binding is metal-ion-dependent, or the use of lifetime-based sensing as in the present invention.

Fluorescence resonance energy transfer is a dipole-dipole interaction described by Förster (Förster, Th. (1948) *Ann. Physik* 2, 55– 75). Förster's theory is very well-established, with thousands of examples in the literature of its predictive power. The rate of energy transfer $K_T$ is a function of the distance between donor and acceptor r, the refractive index of the medium n, the degree of energy overlap J between the emission spectrum of the donor and the absorbance spectrum of the acceptor, the emissive rate of the donor in the absence of acceptor $\lambda_d$, and the relative orientation between the donor and acceptor dipoles $\kappa^2$:

$$K_T = (r^{-6} J \kappa^2 n^{-4} \lambda_d) \times 8.71 \times 10^{23} \text{sec}^{-1}$$

The rate of energy transfer can be simply expressed in terms of a Förster distance $R_0$, which is the distance at which the rates of emission and energy transfer are equal, and the lifetime of the donor $\tau_D$:

$$K_T = \frac{1}{\tau_D} \left[ \frac{R_0}{r} \right]^6$$

A labeled macromolecule such as carbonic anhydrase, wherein the donor fluorophore is approximately at its Förster distance from the azosulfamide in the active site, would exhibit a more rapid apparent decay of its fluorescence due to energy transfer; energy transfer is thus a quenching mechanism, and a decrease in fluorescence intensity should be observed as well. It is well known that by placing the donor much closer to the active site, essentially quantitative quenching results, whereas if the donor is much further away, the quenching is modest due to the sixth power dependence.

It has been demonstrated in the present invention that positioning of the fluorescent donor moiety on the macromolecule at particular distances from a metal ion bound to the macromolecule or an inhibitor bound to the metal ion optimizes the response of the assay.

Thus, it has been found in the present invention, that a sensor, which we term 'fluorescence-based biosensor", transduces the presence or level of the metal ion or ligand as a change in the fluorescence of an indicator phase, which can be measured through a length of optical fiber with the indicator phase at the distal end in contact with a sample containing the metal ion or ligand at the proximal end.

This invention demonstrates for the first time the determination of metal ions and ligands such as anions using a photoluminescent energy transfer mechanism employing a macromolecule. This invention also demonstrates for the first time the importance of controlling the proximity of the photoluminescent-donor-label to the metal ion or ligand in making the determinations.

SUMMARY OF THE INVENTION

Accordingly, an object of the present invention is to provide a method for determining the presence of and quantifying chemical analytes such as metal ions and ligands.

More particularly, it is an object of the present invention to provide a method of detecting and quantifying metal ions or ligands in a sample by measuring changes in photoluminescence resulting from the binding of said metal ion or ligand to a binding site of a suitable photoluminescent-labeled macromolecule, followed by the subsequent and concomitant binding of a colored inhibitor, which quenches the fluorescence of the label on the macromolecule.

Another object of the present invention is to provide a method of quantifying the concentration of metal ions by the energy transfer-induced quenching of a photoluminescent-donor-label.

It is a further object of the invention, to use the same approach as the above method to detect ligands such as $CN^{31}$ by their perturbation of the d—d absorption bands of metals such as Co(II) and Cu(II) when bound in the binding site, as measured by changes in emission from suitable photoluminescent donor label on the macromolecule.

DETAILED DESCRIPTION OF THE INVENTION

Figure 1:
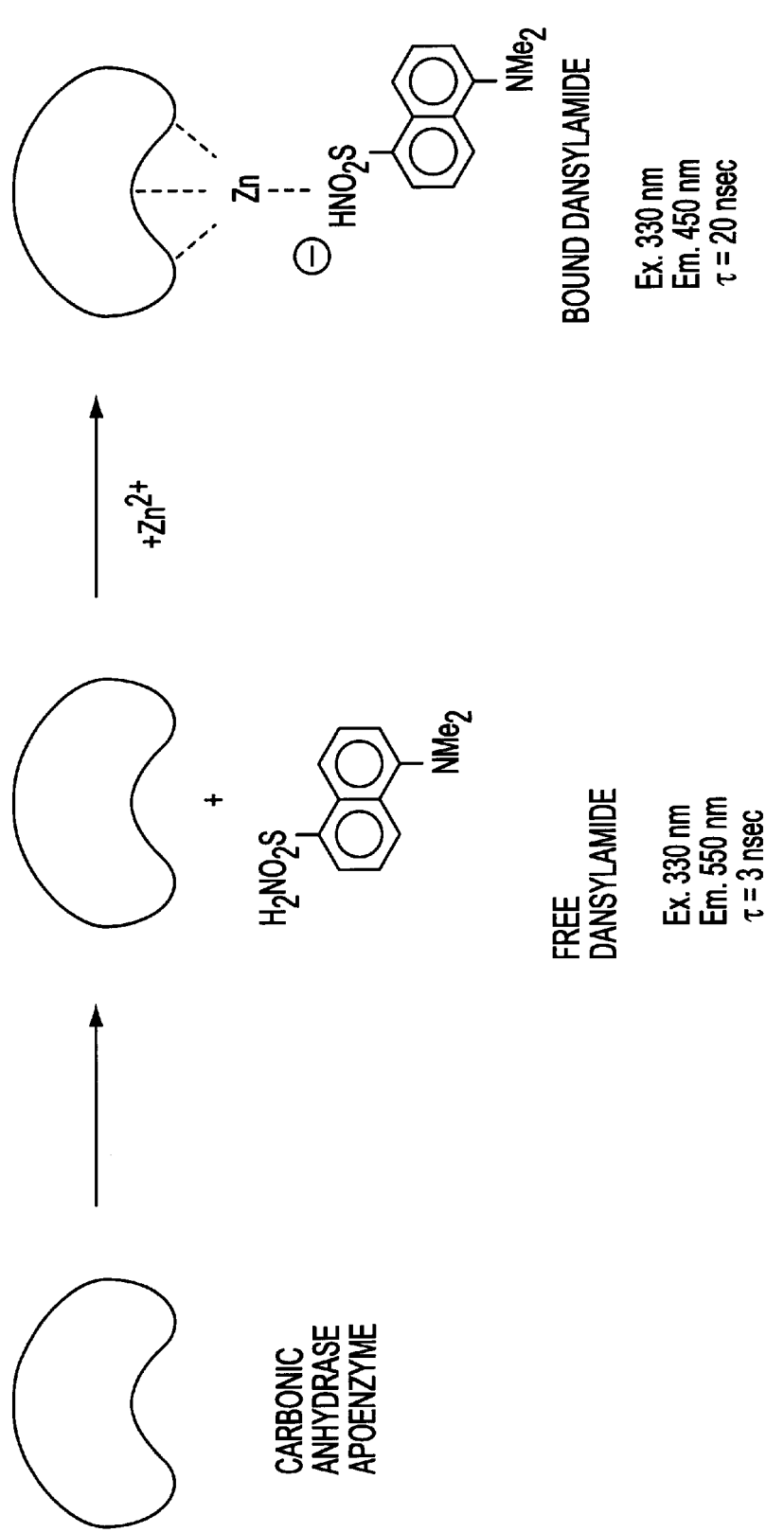
FIG. 1 shows the zinc bio sensor scheme.
Figure 2:
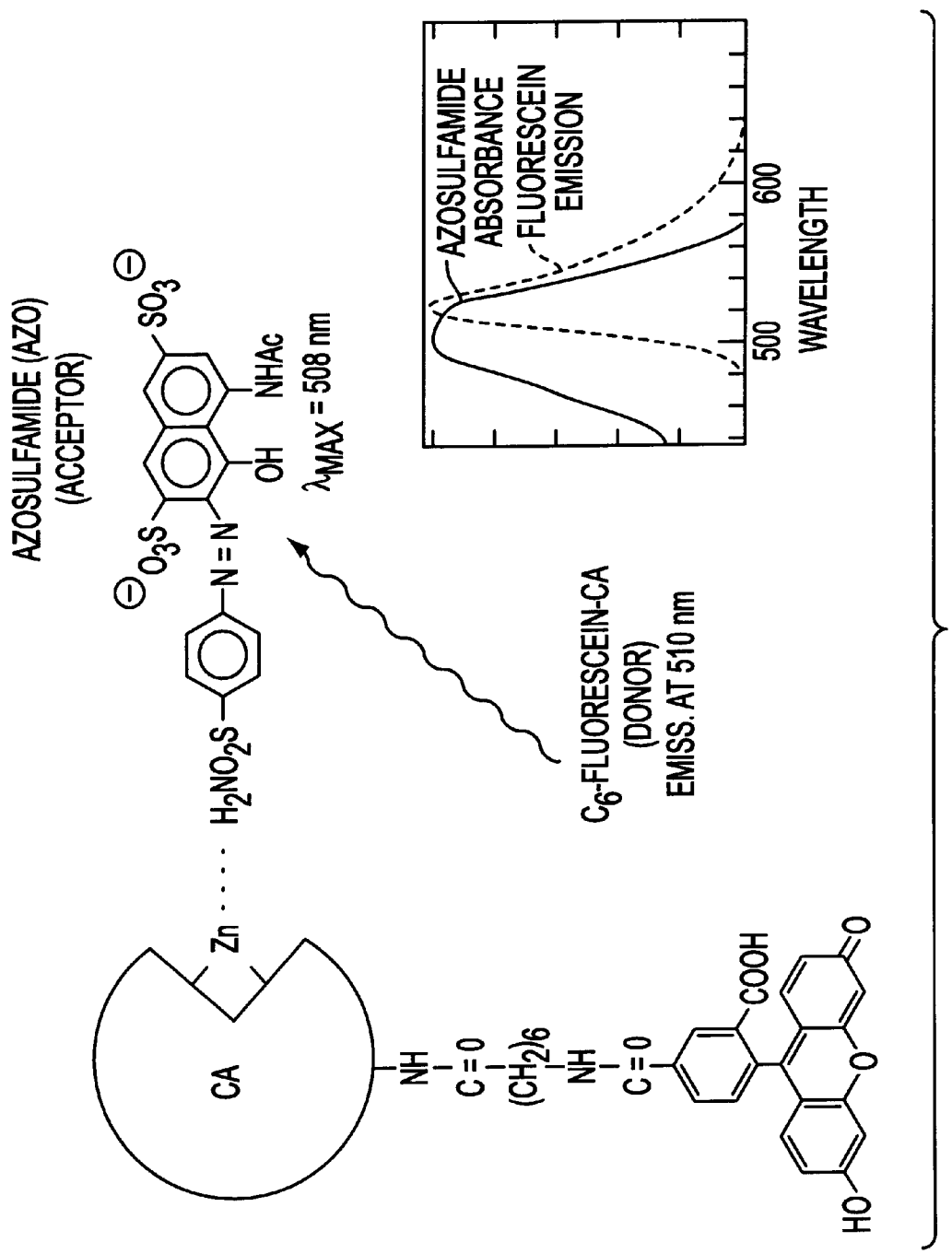
FIG. 2 shows a C6-fluorescein-labeled carbonic anhydrase with $Zn^{2+}$ bound in a metal ion binding site (the enzyme active site in this case).

The present invention demonstrates quantitative photoluminescent quenching as a means of transducing the presence or level of a metal ion or ligand, principally by fluorescence resonance energy transfer. The present invention further demonstrates the use of a colored inhibitor which quenches by energy transfer and which is brought into sufficiently close proximity by serving as an additional ligand on an active site metal.

A macromolecule labeled with a photoluminescent label is mixed with a colored ligand, preferably a colored inhibitor, such as azosulfamide, and its fluorescence decay measured. Photoluminescence is herein defined as the emission of light by a sample, molecule, or a material upon illumination by light, specifically to include fluorescence and phosphorescence. The label may be attached to the macromolecule covalently or non-covalently, or the macromolecule may be intrinsically photoluminescent, as in the frequent case of a protein containing tyrosine or tryptophan. Then a sample possibly containing some amount of a metal ion or ligand to be measured is added and becomes bound to the colored inhibitor, permitting the inhibitor to bind to the fraction of macromolecules having metal ion or ligand in the active site. In ideal circumstances, the inhibitor-bound macromolecule exhibits a significantly faster decay rate than the unquenched donor, resulting in a degree of heterogeneity which may be measured quantitatively in principle from the time-resolved fluorescence.

As a result, quantitative quenching is undesirable because the lack of emission renders the inhibitor-bound macromolecule "silent" from the standpoint of time-resolved fluorometry, even though the steady state intensity shows a large effect. A suitably photoluminescent-labeled macromolecule in aqueous solution would exhibit fluorescence characteristics typical of the label. Adding a colored inhibitor whose binding is metal-dependent at levels up to micromolar has little or no effect on the measured fluorescence lifetime and none on the intensity apart from the inner filter effects. Therefore, some intermediate degree of quenching (and thus spectral overlap and proximity) is desirable.

In the present invention, increasing concentrations of the metal ion or ligand were added to the photoluminescent-labeled macromolecule, resulting in binding of the metal ion or ligand to the macromolecule, and binding of the colored inhibitor to the metal ion. A consequence of the binding is that the bound colored inhibitor is brought in to much closer proximity than on the average as compared to when it is unbound, and as a result partial quenching of the photoluminescent-donor-label on the macromolecule occurs. Consequently, the photoluminescent intensity and lifetime of the photoluminescent donor on macromolecules with bound inhibitor are reduced. Thus as a greater proportion of the macromolecules have a colored inhibitor bound as well as a metal ion. This binding occurs and may be quantitatively predicted according to the metal ions' and colored inhibitors' binding constants and the law of mass action. The proportion of photoluminescence coming from the shorter lifetime, reduced-quantum-yield-bound form would come to predominate, in proportion to the concentration of the metal ion or ligand. Hence the concentration of the metal ion or ligand can be measured.

The choice of macromolecule to be used is not critical to the present invention, as long as a suitable photoluminescent donor label is bound, the photoluminescent donor label is optimally positioned with respect to the metal or ligand binding site, and a metal ion or ligand binding site is present. The donor label is optimally positioned with respect to the metal or ligand binding site. Macromolecules useful in the present invention include, but are not limited to, proteins. Examples include carbonic anhydrase II, alkaline phosphatase, leucine aminopeptidase, carboxypeptidase, laccase, azurin, and urease. Most preferable is carbonic anhydrase II. Mutants or variants of the macromolecule are also envisioned in the present invention. A mutant or variant is a compound which is substantially similar to the macromolecule. A macromolecule is said to be "substantially similar" to another molecule if both molecules have substantially similar structures or if both molecules possess a suitably bound photoluminescent donor label which is optimally positioned with respect to the metal or ligand binding site, and a metal ion or ligand binding site. Thus, a macromolecule is considered a variant or mutant as those terms are used herein even if the structure of one of the molecule is not found in the other, or if the sequence of amino acid residues is not identical. Determination that any of the above listed macromolecules may function in the present invention is easily ascertained by those skilled in the art by methods known in the art.

Also included within the definition of variants of human carbonic anhydrase II are cysteine-substituted forms, such as serine-166, histidine-36, histidine-64, histidine-97, tyrosine-7, valine-143, and leucine-198. Such enzyme variants can be produced by well known methods. One of the advantages of using a binding site incorporated in a macromolecule scaffold such as carbonic anhydrase is that by the use of such site-directed mutagenesis approaches the donor may be placed an ideal distance from the acceptor in the active site. In general, this cannot be done with non-macromolecule binding materials. We have described quantitatively the approach for positioning such donors, (Thompson, et al. *J. Biomed. Opt.* 1(1), 131–137 (1996)) and find that the preferable distance is about 0.75 times the $R_0$, the Förster distance where energy transfer is 50% efficient.

Many photoluminescent donor labels may be selected based upon the metal ion, ligand, and/or mechanism of quenching as set forth hereinunder. Preferred embodiments to be employed in the present invention include, but are not limited to fluorescein isothiocyanate, rhodamine iodoacetamide, CY3 iodoacetamide, Green Fluorescent Protein, morpholinorhodamine iodoacetamide, pyrene propylmaleimide, nitrobenzooxazolyl chloride, CY5-iodoacetamide, 4-sulfobenzoxazolyl fluoride, monobromobimane, and bodipyiodoacetamide. Many fluorescent labels are known in the art (R. P. Haugland and K. Larison, Handbook of Fluorescent Probes 1994–5, Molecular Probes, Eugene Oreg.). Many other fluorescent labels are disclosed in the literature, as well as the intrinsic tyrosyl and tryptophanyl fluorescence of the protein, and phosphorescent labels are considered within the scope of this present invention.

The metal ion to be detected by the present invention includes, but is not limited to Zn(II), Co(II), Cd(II), Ni(II), Hg(II), Fe(II), Mn(II), Pb(II), and Cu(II). Other metal ions are known by those skilled in the art which bind to macromolecules with greater or lesser affinity and which quench fluorescence themselves or promote the binding of colored inhibitors which can quench the photoluminescence.

The measurement of quenching can be determined by techniques well known to those in the art, including measuring the change in fluorescence lifetime, fluorescence intensity, excitation spectrum of the donor, fluorescence dichroism, or phosphorescence intensity or lifetime. The preferred embodiment of this invention is to measure the change in fluorescence lifetime which provides a more precise, artifact-free, and photobleaching-free measurement than other methods. More particularly, the measurement is of the change in the proportion of short lifetime emitters corresponding to the metal-ion or ligand bound form of the macromolecule. It is also preferable to measure these time-dependent changes by phase fluorometry, which is also called phase-modulation fluorometry, or frequency-domain fluorometry. The proportion of short lifetime emitters attributed to the bound form of the macromolecule can be correlated with a unique phase angle and demodulation ratio at some suitable modulation frequency. The proportions of each form (bound vs. unbound) can be determined by measuring phase shifts and demodulations over a suitably wide range of frequencies and fitting them to decay law (Lakowicz, J. R. and I. Gryczynski, "Frequency-Domain Fluorescence Spectroscopy," in *Topics in Fluorescence Spectroscopy Vol I: Techniques* J. R. Lakowicz, ed.) New York, Plenum Press, pp. 293–336).

Figure 16:
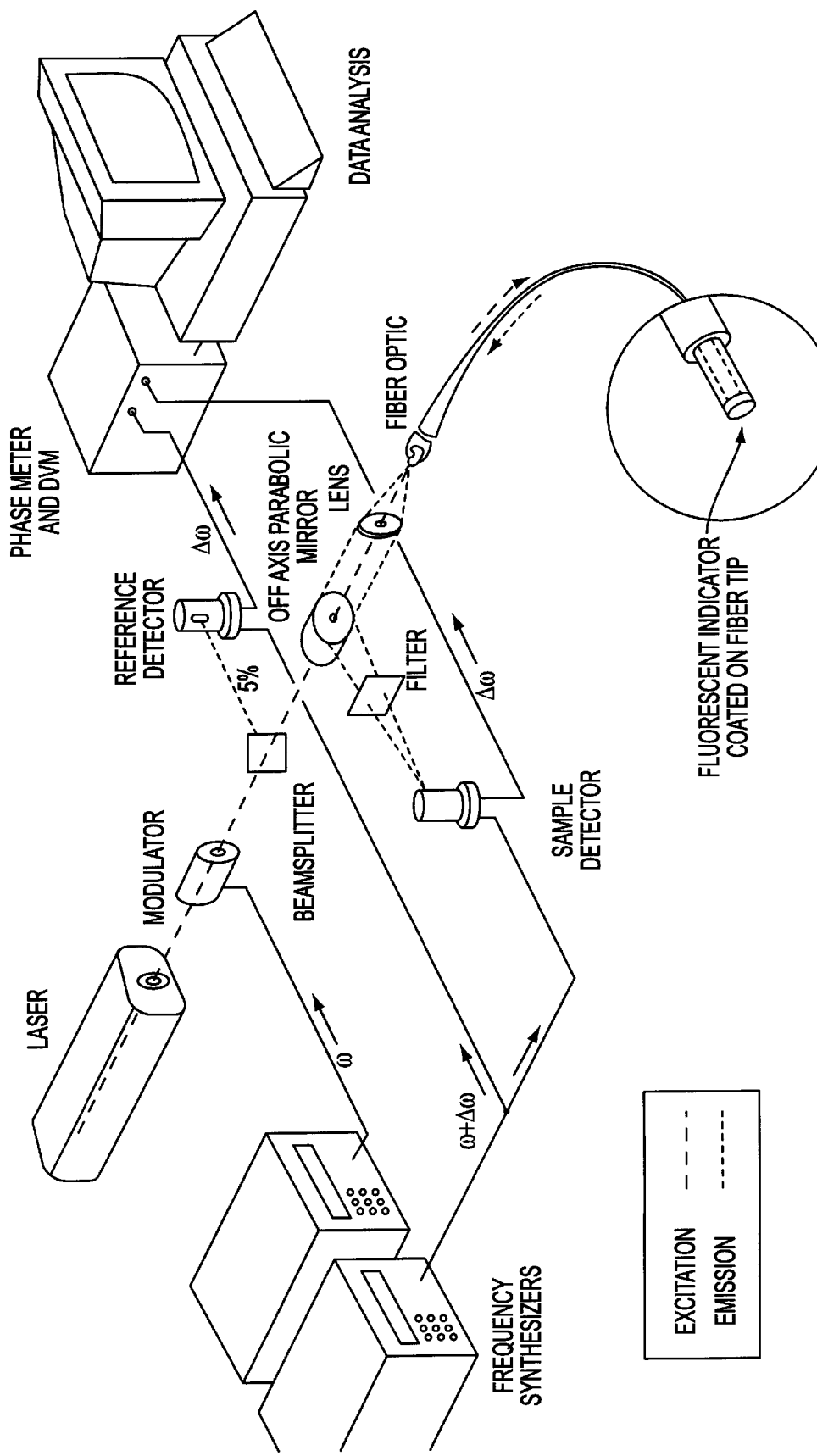
FIG. 16. Apparatus for lifetime-based fiber optic biosensors.

Many techniques are known to the art for measuring the time dependence of fluorescence emission, including streak cameras, time correlated single photon counting, direct measurement of the time resolved fluorescence, upconversion techniques, phase-sensitive detection, boxcar techniques, and the like. Similarly, while lasers as light sources and photomultiplier tubes as detectors have been used, for some applications adequate or improved performance may be achieved by the use of LED's, laser diodes, electroluminescent sources, arc lamps, spark gaps, xenon arc lamps, incandescent lamps, or other sources. In the same fashion other light detectors may be used, including microchannel plate photomultiplier tubes, photodiodes, avalanche photodiodes, streak cameras, CCD's and other detectors known to the art may be used. The apparatus for lifetime-based fiber optic biosensing is depicted in FIG. 16. Fundamentally, this device is a phase fluorometer adapted for measurements through a length of optical fiber. Excitation from the laser (dashed line) is amplitude modulated at 1–250 MHz by an E-O modulator; a beam splitter takes 5% of the excitation to measure the phase and modulation. The excitation is launched into the fiber optic by the lens whence it excites the fluorophores in the tip coating; the fluorescence is coupled back into the fiber and exits the proximal end (dotted line). The fluorescence is reflected off the off-axis parabolic mirror into the detector, which measures its phase and modulation relative to the excitation.

In the present invention, quenching occurs due to proximity of the metal ion or ligand to the photoluminescent donor label. In some embodiments, this proximity-dependent quenching is facilitated by the use of colored inhibitors. A subset of metal ions which bind to the active site of a macromolecule are transduced via the proximity of a bound colored inhibitor. Many inhibitors of the preferred macromolecule carbonic anhydrase are known to the art, including many aryl sulfonamides. These compounds are quantifiable by one of the methods described, and they can be made to exhibit some proximity-dependent fluorescence quenching. Thus other colored aryl sulfonamide inhibitors known to the art such as 4-(4'dimethylaminophenyl) azophenyl sulfonamide and salicylazobenzensulfonamide are also workable in some circumstances discernable to one of ordinary skill in the art. The use of azosulfamide as a colored ligand bound to the macromolecule is the preferred embodiment when the metal ion to be measured is Co(II), Cd(II), or Zn(II).

Other methods of proximity-dependent quenching are utilized depending on the metal ion or ligand to be transduced. Several metals exhibit weak d—d absorbance bands which can undergo characteristic changes upon binding to the active site of the macromolecule. Metals known to do this include Ni(II), Co(II), and Cu(II) (S. Lindskog, L. E. Henderson, K. K. Kannan, A. Liljas, P. O. Nyman, and B.

Figure 3:
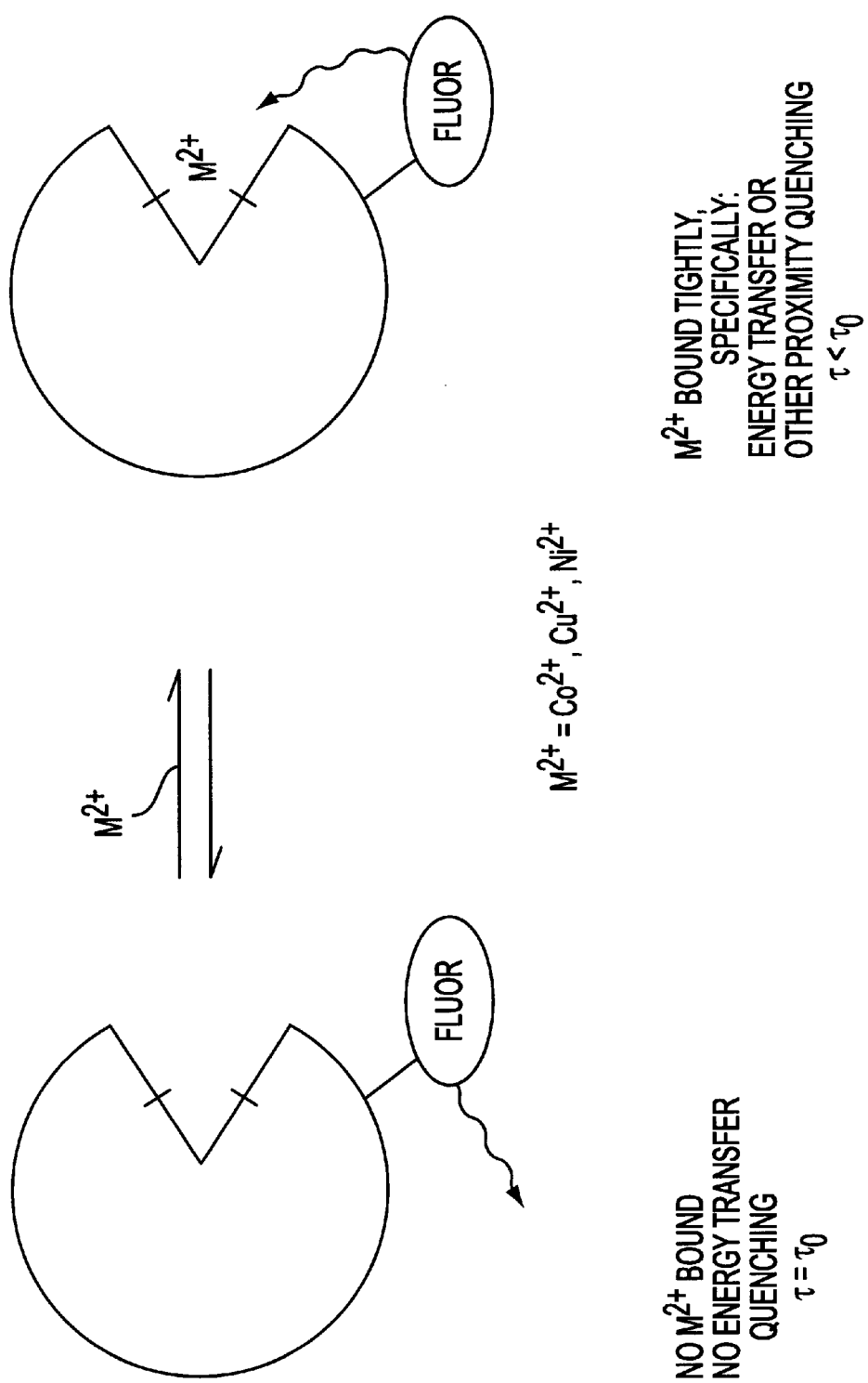
FIG. 3 shows the exchange between apo-carbonic anhydrase and "holo"-carbonic anhydrase.

Strandberg, "Carbonic Anhydrase," in *The Enzymes*, Vol.5, Third Ed. (P. D. Boyer, Ed.) pp. 587–665 (1971)). Such absorbing species can serve as energy transfer acceptors for a fluorescent donor with suitable position, orientation, and spectral overlap, and thus transduce their binding by the macromolecule as a change in fluorescence intensity and lifetime of such a donor (FIG. 3). Demonstration of such sensing in solution and through a fiber optic is shown in R. B. Thompson, Z. Ge, M. W. Patchan, and C. A. Fierke, "Energy transfer-based fiber optic metal ion biosensor," Proc. SPIE Conf. Advances in Fluorescence Sensing Technology (SPIE Vol. 2388) G. R. Lakowicz, ed.), pp. 138–147 (1995); R. B. Thompson, Z. Ge, M. W. Patchan, C. -C. Huang, and C. A. Fierke, Biosensors & Bioelectronics, 11(6/7), pp. 557–564 (1996). In this case no separate colored inhibitor is necessary.

Other metals that do not absorb light but bind to the active site of the macromolecule could also be transduced in this manner in a competition-type assay. Such assays are well known in the art. While the results obtained in the present invention are consistent with the well-established theory of Förster energy transfer, other proximity-dependent quenching processes to the observed response are envisioned by the present invention.

Typical metallochromic indicators such as bathophenanthroline or Ferrozine, which have been well known to the art for fifty years typically have extinction coefficients with the metal ion 100-fold greater than the d—d absorbance of the metals themselves. Also, while carbonic anhydrase exhibits intrinsic ultraviolet tryptophanyl fluorescence (like nearly all other proteins), it does not ordinarily emit in the visible regime where the principal d—d absorbance bands are to be found, and there is no observation or measurement of energy transfer to the d—d absorbance band of a suitable metal ion bound to a protein. The lanthanides, Eu(III), Tb(III), Dy(III), Sm(III), can serve as energy transfer acceptors but they do not exhibit d—d absorbance bands perturbed by binding, and we know of no quantitation of lanthanides by this means.

The metallo-macromolecule of the present invention is used in the same manner as described above for the macromolecule. Accordingly, the macromolecules useful in the metallo-macromolecule include but are not limited to proteins. The resultant metallo-macromolecule thus may comprise a metallo-enzyme. Such metallo-molecules include, but are not limited to, carbonic anhydrases with the d—d absorbing metal ions Cu(II), Co(II), or Ni(II) already bound to the active site. It is to this metallo-molecule that an unknown ligand to be detected is bound, resulting in complexes such as but not limited to metallo-enzyme-ligand complexes.

Figure 4:
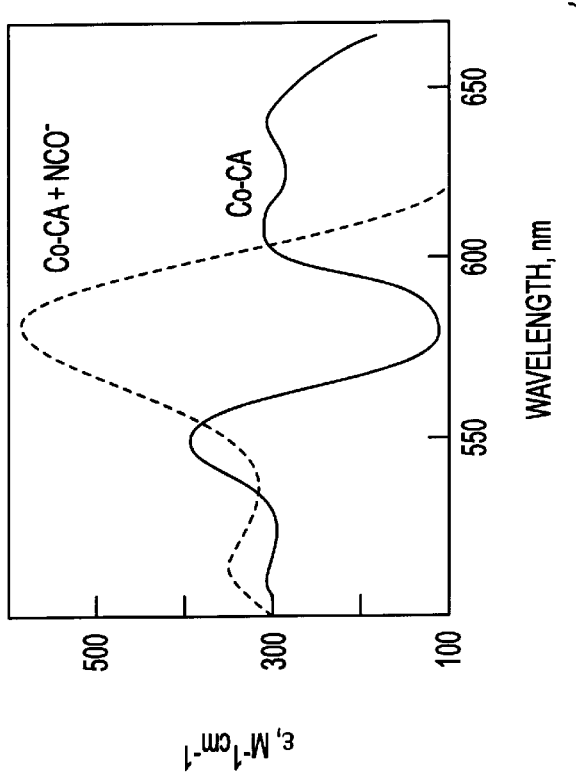
FIG. 4 shows the carbonic anhydrase-based biosensing of anions.
Figure 4:
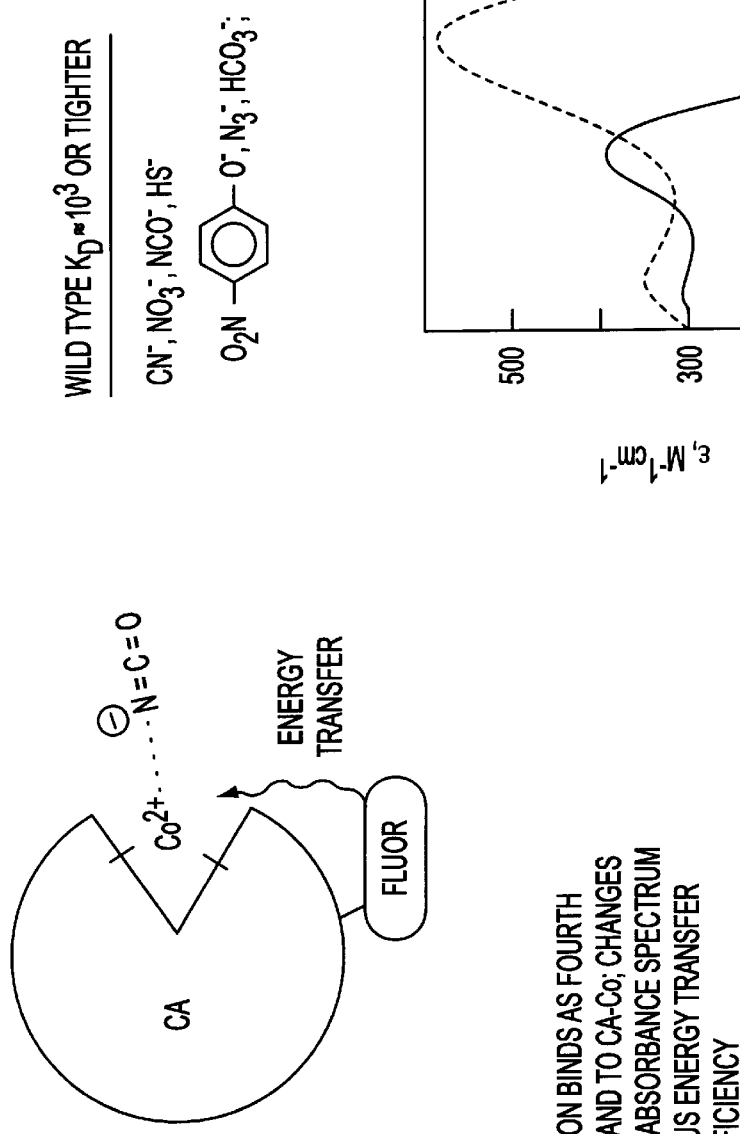

The ligands to be detected include, but are not limited to OH$^-$, N$_3^-$, CN$^-$, CNO$^-$, NO$_3^-$, acetate, formate, HCO$_3^-$, phenolate, dinitrophenolate, HS$^-$, or NO$_3^-$, It is well known to those skilled in the art that many anionic molecules are capable of binding (in some cases as a fourth ligand to the active site metal) to carbonic anhydrases such that they inhibit the activity of the holoenzyme. In the cases of Co(II), Ni(II), and Cu(II) (the latter of which has no activity), the characteristic d—d absorbance spectrum of the metal is perturbed to some degree when anions such as become bound to the active site. This perturbation of absorbance can be significant, such that for a suitably chosen photoluminescent donor the energy transfer efficiency to the metal may be altered significantly (FIG. 4).

For instance, a donor exhibiting emission at 640 nanometers and positioned such that it would transfer some portion of its energy to Co(II) in the active site would exhibit a shortened lifetime. If cyanate ion were added in sufficient amount (concentrations in the micromolar to millimolar ranges) the cyanate becomes bound to the Co(II) in the active site as a fourth ligand, the ligand field changes, which results in almost complete elimination of absorbance at 640 nanometers, resulting in reduced energy transfer with a concomitant increase in the fluorescence intensity and lifetime of the bound form, which may be quantitated by phase fluorometry or another suitable method.

Different anions will have different effects depending on their measured perturbations to the absorbance spectrum of the bound metal, which may be predicted on the basis of the well-known theory of energy transfer and the known emission and absorbance spectra. Similarly, the spectral output of the donor can be chosen to maximize the perturbation of energy transfer upon anion binding.

Furthermore, other proximity-dependent quenching effects promoted by a colored ligand or metal-ion binding may be used and are considered within the scope of the present invention. Such proximity-dependent quenching processes include atom-based quenching, quenching by paramagnetic ions, quenching by nitroxide spin labels and other free radicals, and quenching by electron transfer.

Thus, we have demonstrated that metal ion-dependent changes in the lifetime of a fluorescent-labeled enzyme can be used to sense the presence and levels of metal ions in solution through an optical fiber.

The following examples are provided for illustrative purposes only, and are not intended to limit the scope of the present invention.

EXAMPLE 1

Human carbonic anhydrase II (recombinant) was a gift from Dr. Carol Fierke of Duke University, or purchased from Sigma, and zinc was removed from it quantitatively as previously described (Thompson, R. B. and Patchan, M. N. (1993) in *Proc. of the SPIE Conference on Chemical, Biochemical, and Environmental Fiber Optic Sensors V.* Lieberman, R. A. (Ed.) pp. 296–306. Society of Photooptical Instrumentation Engineers, Bellingham, Wash.). The succinimidyl esters of 5-(and 6-)carboxyfluorescein (C-1311); 5-(and 6-)carboxytetramethylrhodamine (C-1171); 7-diethylaminocoumarin-3-carboxylic acid (D-1412), and 6'-(fluorescein-5-(and 6-)carboxamido)hexanoic acid (F-2181) are all products of Molecular Probes, Eugene, Oreg. Azosulfamide (C.A. registry no. 133-60-8, disodium 2-(4'-sulfamylphenylazo)-7-acetamido-1-hydroxynaphthalene-3,6-disulfonate) is from Sigma (A-2759).

Holo-carbonic anhydrase (2 mg) was derivatized with each of the fluorescent succinimidyl esters by treatment with a ten-fold molar excess of the reagent over carbonic anhydrase at pH 9.0 for 1.5 hr. at room temperature. This technique and other similar techniques are well-known (Haugland, chap 2). In some cases equimolar amounts of azosulfamide were added to the reaction mixture to minimize derivatization of residues in the active site and concomitant prevention of azosulfamide binding.

Reactions were quenched by addition of 1 M tris-(hydroxymethyl) aminomethane, unattached reagent was removed by gel filtration, and the average number of fluorophores per enzyme molecule was determined by absorbance using the known visible extinction coefficients of the derivatives (Haugland, R. P. (1992) *Handbook of Fluorescent Probes and Research Chemicals*, Molecular Probes, Eugene, Oreg.) together with a Bradford protein assay (Bio-Rad) using carbonic anhydrase as a standard.

Absorbance spectra were obtained on a Hewlett/Packard 8452A spectrophotometer, and emission spectra were obtained on an SLM 8000c fluorimeter. Frequency-dependent phase shift and demodulation measurements were obtained on an ISS K2 phase fluorometer using a Liconix 4214NB HeCd laser emitting typically 15 mW at 442 nanometers for exciting the fluorescein and rhodamine derivatives and 3 mW at 326 nanometers for exciting the coumarin derivatives as previously described (Thompson, R. B., and Gratton, E. (1988) *Anal. Chem.* 60, 670–4.).

EXAMPLE 2

Figure 5:
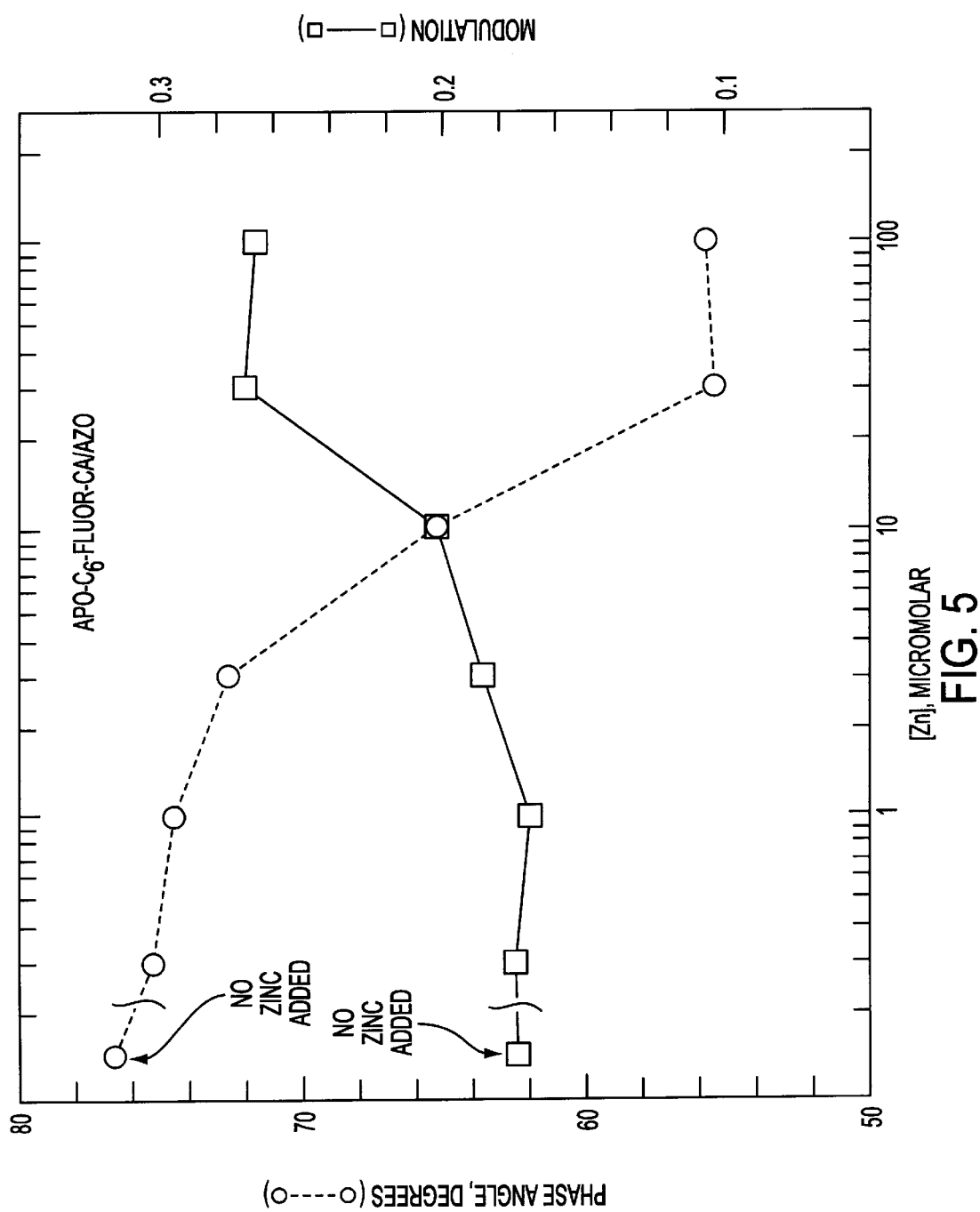
FIG. 5 shows phase shifts (circles) and demodulations (squares) measured for C6-fluorescein-labeled apocarbonic anhydrase in the presence of azosulfamide at 250 MHz as a function of concentration of added zinc.

Phase shifts (circles) and demodulations (squares) were measured for $C_6$-fluorescein-labeled apocarbonic anhydrase in the presence of azosulfamide at 250 MHz, as a function of the concentration of added zinc. See FIG. 5.

EXAMPLE 3

Figure 6:
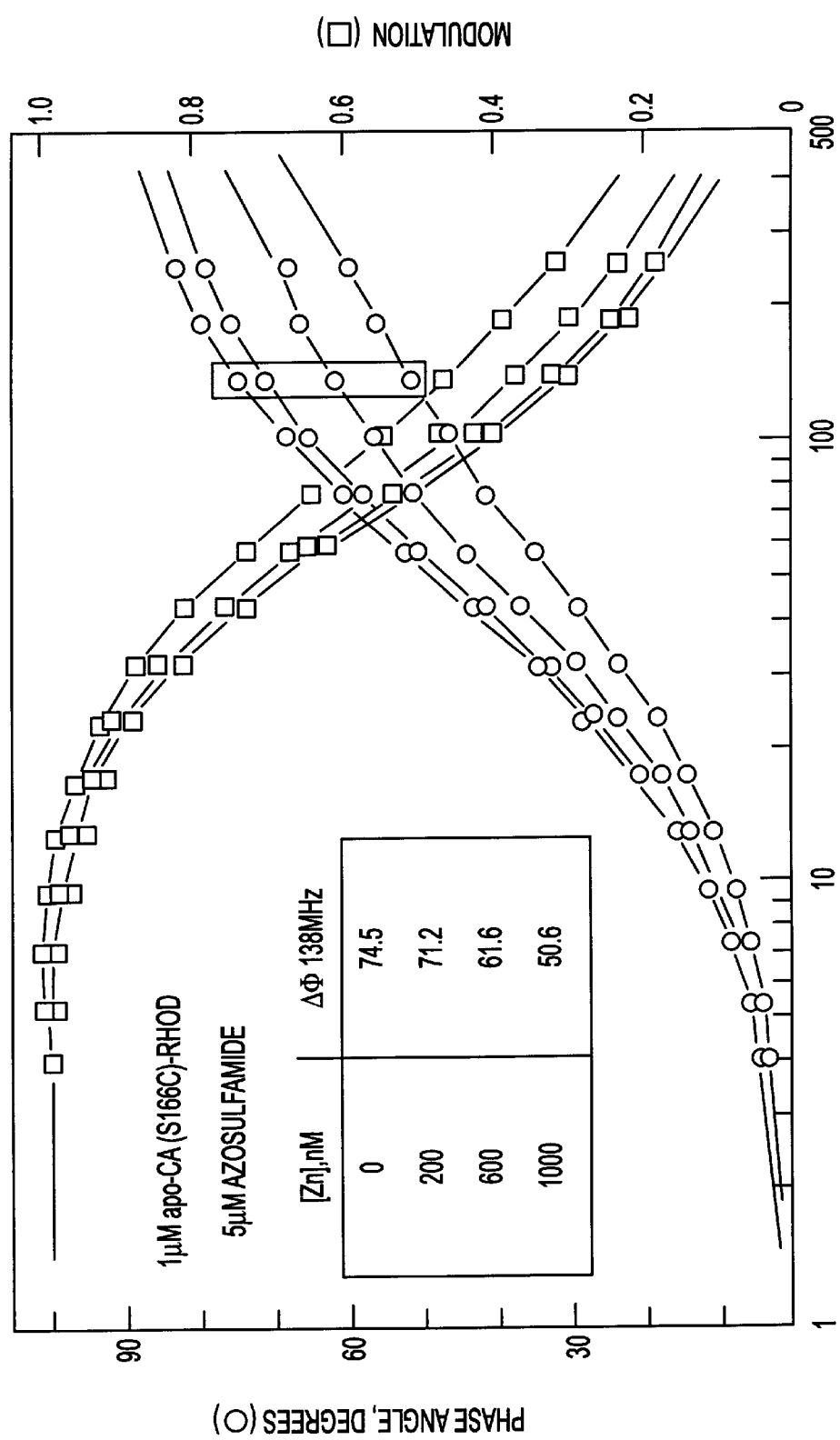
FIG. 6 shows frequency-dependent phase shifts (circles) and demodulations (squares) for mutant (S166C) rhodamine-labeled carbonic anhydrase (1 $\mu$M) with 5 $\mu$M azosulfamide as a function of zinc concentration. The inset gives measured phase shifts at 138 MHz for different concentrations of zinc.

Frequency-dependent phase shifts (circles) and demodulations (squares) were measured for mutant (S166C) rhodamine-labeled carbonic anhydrase (1 ug) with 5 uM azosulfamide as a function of zinc concentration. The inset gives measured phase shifts at 138 MHz for different concentrations of zinc. (Data points enclosed in box). See FIG. 6.

EXAMPLE 4

The principle of energy transfer biosensing of metal ions without a separate colored inhibitor is demonstrated. Wild type human carbonic anhydrase and an H64C variant of human carbonic anhydrase were isolated from *E.coli* strain BL21(DE3)pACA. Following induction of expression the enzyme was purified to greater than 95% homogeneity by chromatography successively on DEAE-SEPHACEL AND S-SEPHAROSE stationary phases, as previously described (Alexander et al., Biochemistry 32:1510 (1993)). The enzyme was fluorescent-labeled at primary amines by reaction with excess CY-5 n-hydroxysuccinimide (Biological Detection Systems, Pittsburgh, Pa.), or at the sulfhydryl introduced at position 64 with excess CY-3 iodoacetamide (BDS) at pH 8.0 or higher for 4 hours in the dark. It is noted that cysteine 206 in the wild type enzyme is generally unreactive to these reagents and these conditions were chosen to minimize reaction with histidine. Unreacted dye was removed by exhaustive dialysis, and the degree of labeling characterized by spectrophotometry (CY-3: e=150,000 $M^{-1}$ $cm^{-1}$ at 550 nm; CY-5: e=250,000 $M^{-1}$ $cm^{-1}$). Derivatives of H64C with cationic (rhodamine) or hydrophobic (BODIPY) reactive dyes were unstable and precipitated rapidly; the CY-3 derivative, where the fluorophore is a dianion, was most stable. Experiments were carried out in 50 mM HEPES pH 7.3, 150 mM sodium sulfate. Steady state fluorescence measurements were performed on an SLM 8000c fluorometer, and lifetime data were acquired on an ISS K2 multifrequency phase fluorometer with an air-cooled argon ion laser emitting 20 mW at 514 nm (Omnichrome), a Liconix 4214NB HeCd laser emitting 5 mW at 442 nanometers, or a directly modulated Toshiba TOLD 9211 laser diode emitting 3 mW at 655 nanometers providing excitation. Frequency-dependent phase shifts and demodulations were measured in cuvettes using Rose Bengal or a scatterer as a reference or through optical fiber (200 um core silica-clad silica, General Fiber Optics catalog no. 16-200S) as previously described (Thompson, R. B., and Lakowicz, J. R. (1993) "Fiber Optic pH Sensor Based on Phase Fluorescence Lifetimes," *Analytical Chemistry* 65, 853–6.)

Figure 8:
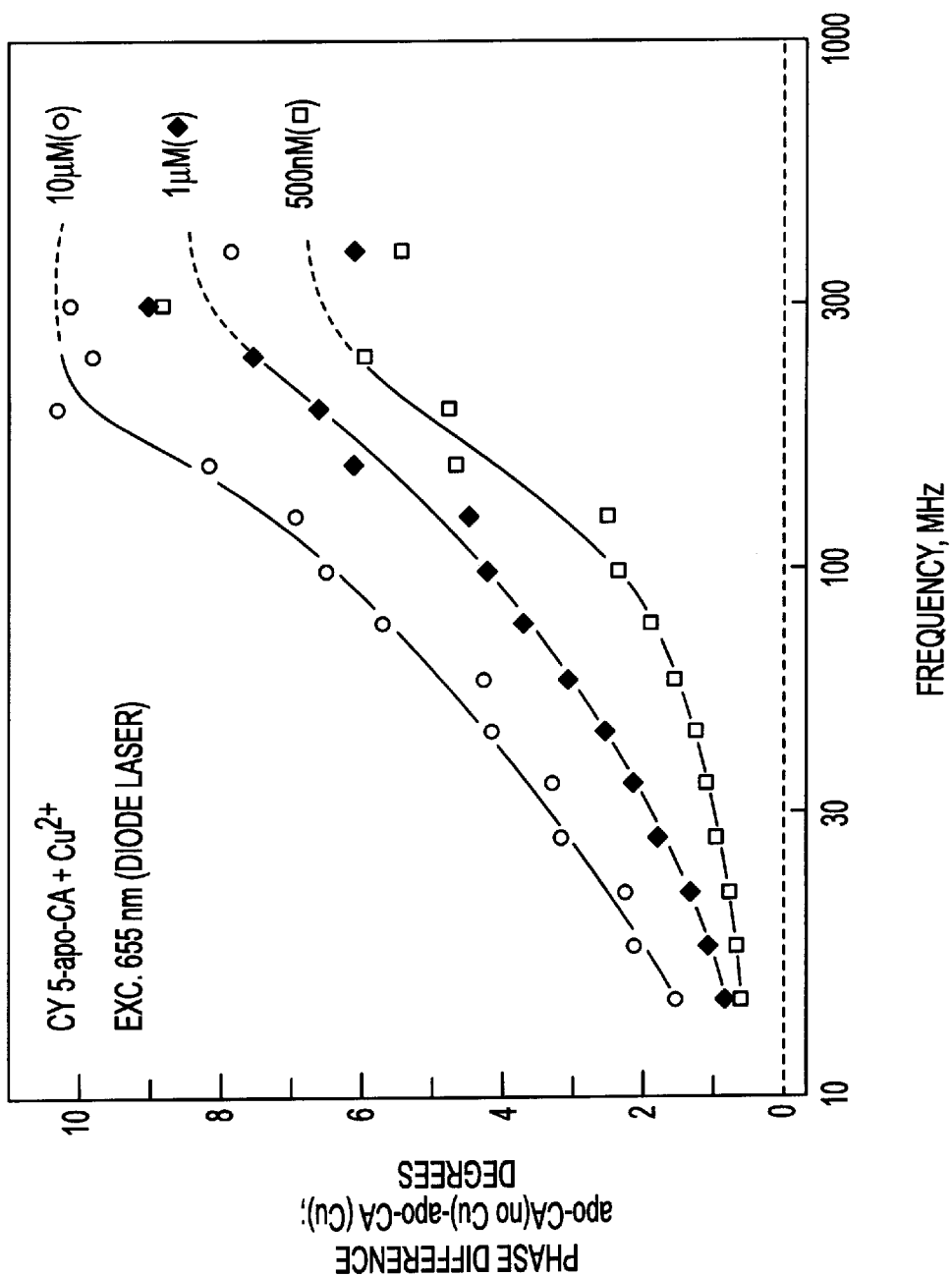
FIG. 8 shows frequency-dependent phase shifts of CY-5-labeled apocarbonic anhydrase for different concentrations of copper.

We have demonstrated that the donor should be a distance r away from the acceptor such that $r \leq 0.75 R_0$, where $R_0$ is the Forster distance where transfer is fifty percent efficient. For CY3 and CY5, the $R_0$'s with Co-CA and Cu-CA are 20.8 and 20.5 Angstroms, respectively. The measured distance from the imidazole ring nitrogens to the zinc ion in the crystal structure is approximately 8 Angstroms, but note that the acetamido moiety of the CY3 label moves the fluorophore away somewhat from the alpha carbon of the residue at position 64 (now a cysteine in this variant) such that the distance of the fluorescent label from the metal ion is now probably closer to 13–15 Angstroms. We derivatized the wild type human CA with the deep red amine-reactive dye CY-5, and after removal of the active site zinc, we measured frequency-dependent phase shifts and demodulations for the protein in the presence of (substoichiometric) concentrations of $Cu^{2+}$; the results are depicted in FIG. 8. Evidently the addition of $Cu^{2+}$ resulted in reduction of the lifetime at concentrations far lower ($\leq 10$ uM) than would be capable of causing simple collisional quenching with this short-lived (1.6 nsec) fluorophore according to the Stern-Volmer theory. Similarly, it seems likely that $Cu^{2+}$ bound to the CY-5 itself would cause quantitative quenching of the fluorophore (static quenching), resulting in no apparent change in the lifetime Consequently, we conclude that the copper is bound to the protein, resulting in partial quenching when bound, and with a binding constant of micromolar or tighter (the binding constant of $Cu^{2+}$ to human CA II is about 0.1 picomolar). Thus these results are consistent with the copper ion binding at the active site and partially quenching the CY-5 by energy transfer. Employing site-directed mutants is desirable in this case as the random nature of derivatizing the primary amines on the outside of the molecule makes it difficult to reproducibly synthesize the CY-5 derivative.

Figure 7:
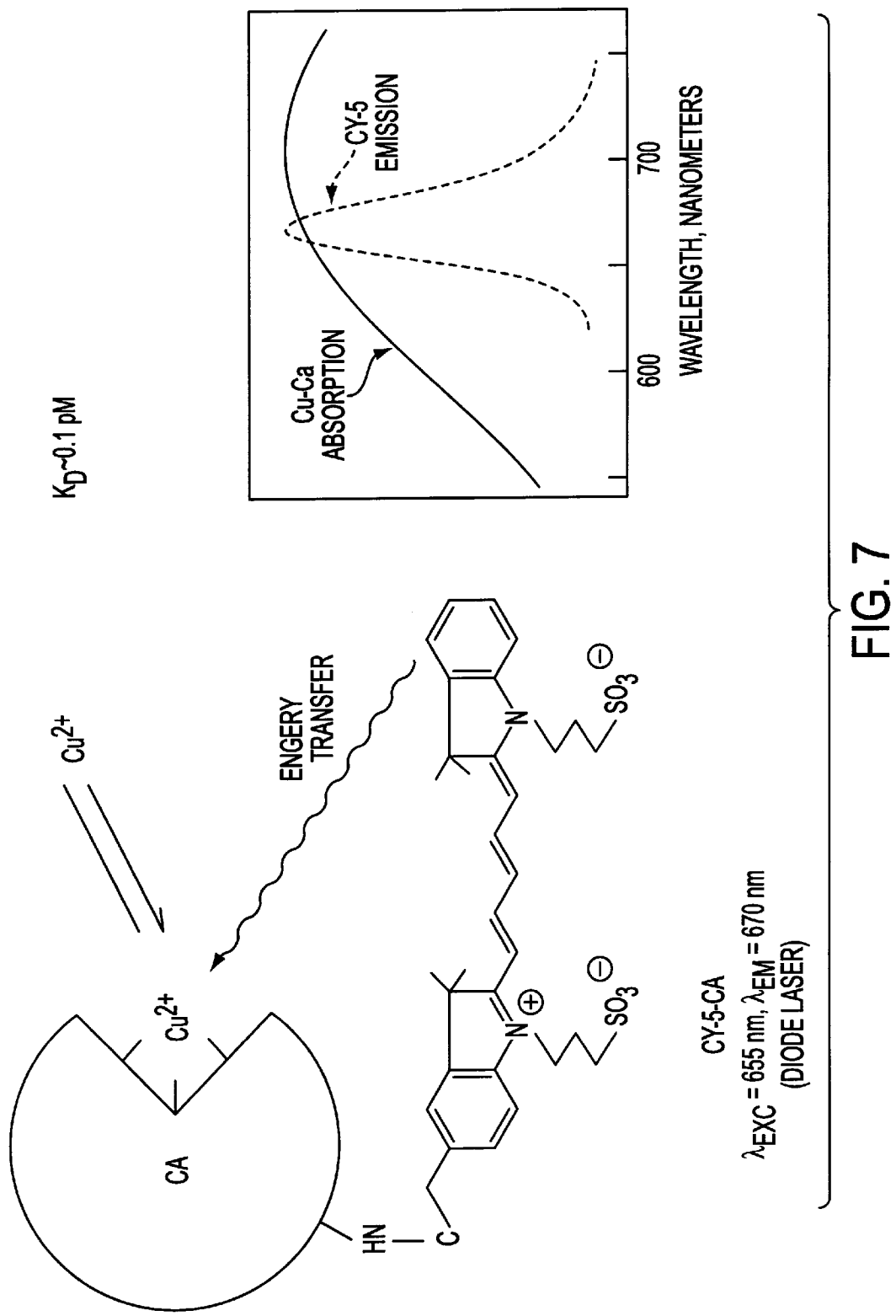
FIG. 7 shows the principle of energy transfer biosensing of metal ions without a separate inhibitor. The CY-5-labeled apo-carbonic anhydrase exhibits unquenched emission in the red; when copper binds in the active site, its weak visible-NIR absorbance quenches the CY-5 emission by energy transfer, reducing the CY-5 intensity and lifetime.

The CY-5-labeled apo-carbonic anhydrase exhibits unquenched emission in the deep red; when copper binds in the active site, its weak visible-NIR absorbance quenches the CY-5 emission by energy transfer, reducing the CY-5 intensity and lifetime. See FIG. 7.

EXAMPLE 5

Phase angles measured at 250 MHz for H64C-CY-3-apoCA entrapped in 5% polyacrylamide gel at the distal end of a 1.5 meter optical fiber as a function of time are exemplified; the fiber tip was dipped in buffered solutions of 2 uM (squares) and 200 nM (circles) $Co^{+2}$. See FIG. 9.

A variant of CA, H64C, was chosen which provided very close (9 Angstroms from the metal) placement of the fluorescent donor. The incorporated cysteine thiol provided facile derivatization with iodoacetamide derivatives; we note that the other cysteine present in wild type enzyme, cysteine 206, is unreactive to such reagents. The variant was derivatized with one of two fluorescent reagents, fluorescein iodoacetamide and CY-3 iodoacetamide. After removal of zinc, the frequency-dependent phase shifts and demodulations of each were measured as a function of added $Co^{2+}$; the results for the CY-3 derivative (H64C-CY3-apoCA) are depicted in FIG. 9.

Figure 9:
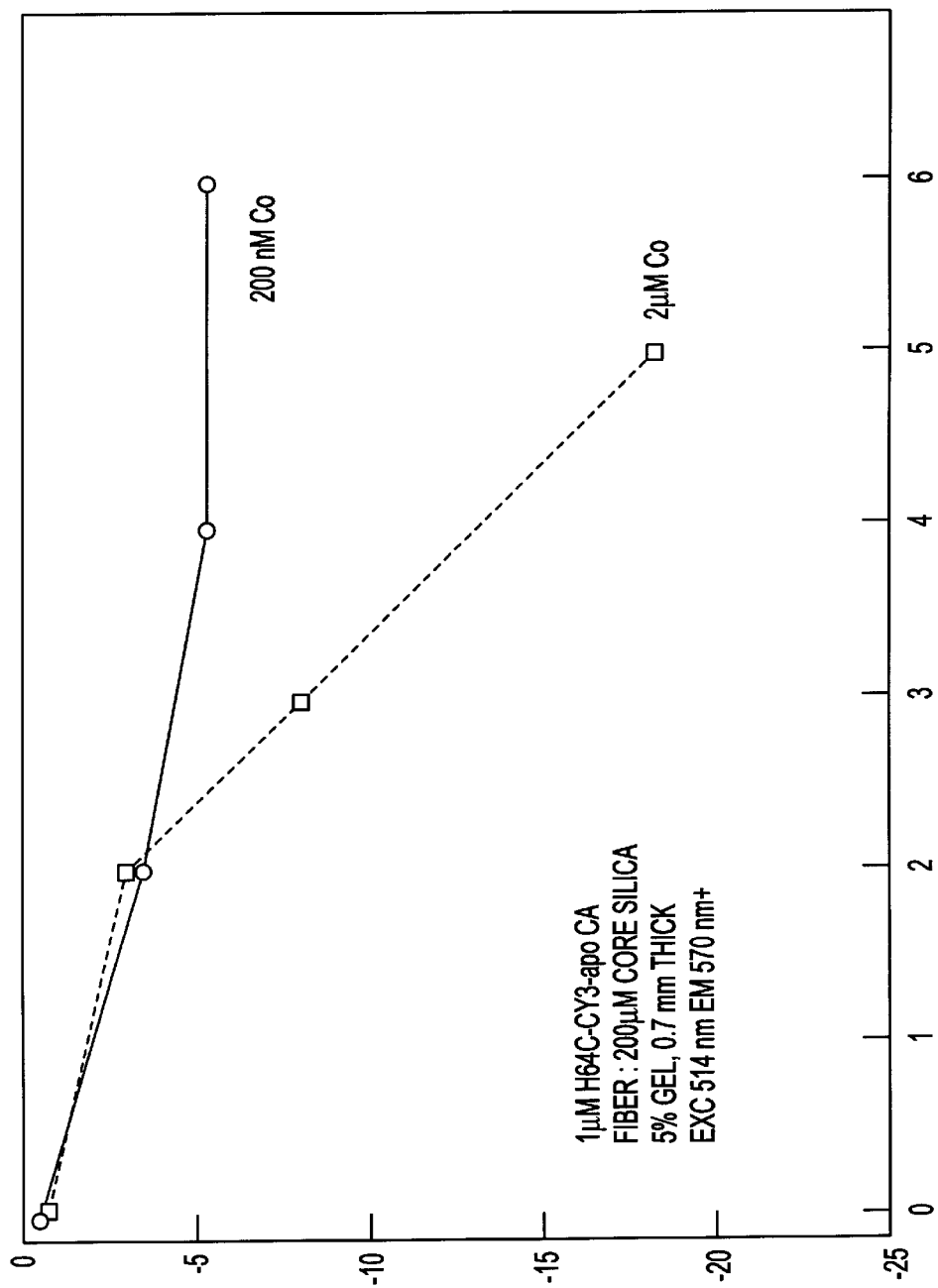
FIG. 9 shows phase angles measured at 250 MHz for H64C-CY-3-apoCA entrapped in 5% polyacrylamide gel at the distal end of a 1.5 meter optical fiber as a function of time; the fiber tip was dipped in buffered solutions of 2 uM (squares) and 200 nM (circles) $Co^{+2}$.
Figure 10:
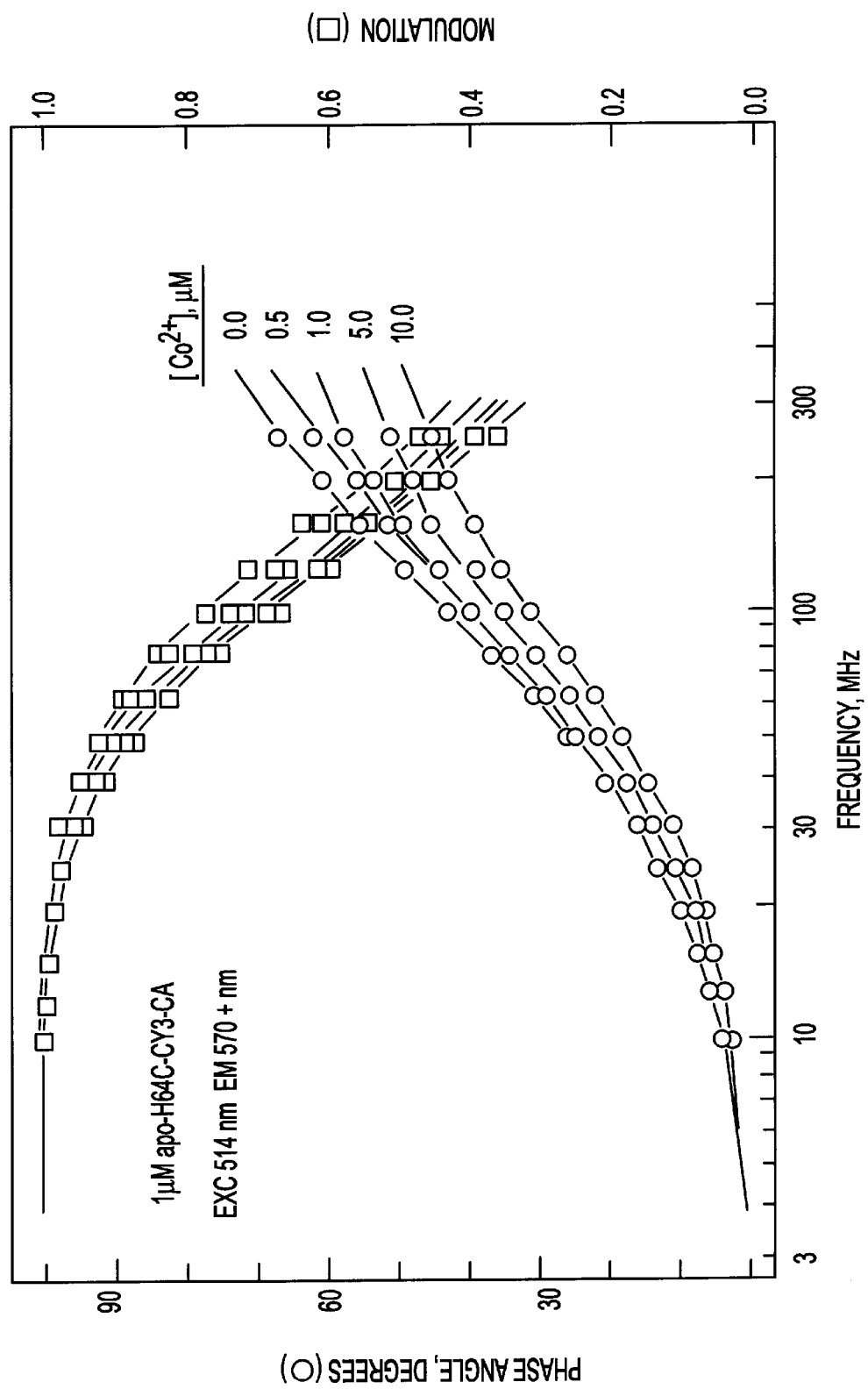
FIG. 10. Frequency-dependent phase angles and demodulations of H64C-CY-3-apocarbonic anhydrase measured in the absence and presence of varying concentrations of $Co^{+2}$.

For an energy transfer-based transducer the response of H64C-CY3-apoCA to $Co^{2+}$ is very good: the phase angles change over thirty degrees at 250 MHz as the concentration of $Co^{2+}$ is increased (FIG. 9). We note that the wild type binding constant for $Co^{2+}$ is in the nanomolar range, therefore we expect to see the system saturate around micromolar concentration when the apoenzyme is present at one micromolar. In fact, we see a rapid drop in phase angle with metal ion concentration up to micromolar concentration, with a less marked drop at higher concentrations (FIG. 10). We also measured the effect of cobalt concentration on the holoenzyme, that is, where the zinc ion has not been removed from the active site. Ideally, one expects no response to increasing cobalt concentration since the active site is already occupied by $Zn^{2+}$ and zinc exchange is extremely slow at this pH. While the steep drop at lower concentrations was much reduced, there remained a modest decline in phase angle at higher concentrations. We suspect that the enzyme may have other, lower affinity sites for cobalt which may contribute to the response at higher concentrations; such binding to CA has been detected by other means (C. -C. Huang and C. A. Fierke, unpublished observations). It is known that other metal ions such as Hg or Pb bind at sites other than the active site, particularly at cys-206 (Eriksson, E. A., Jones, T. A., and Liljas, A. (1986) "Crystallographic studies of human carbonic anhydrase II," in *Zinc Enzymes* (I. Bertini, C. Luchinat, W. Maret, and M. Zeppezauer, eds.) Boston: Birkhauser, pp. 317–328.)

The CY3-labeled H64C variant exhibits differing fluorescence lifetimes in the holo- and apo-forms (note the zero $Co^{2+}$ concentration points in FIG. 10). Notwithstanding the shorter apparent lifetime of the holo form (1.46 nsec, results not shown) compared to the apo form (1.76 nsec), we do not believe zinc ion per se quenches the emission of CY3 based on its known behavior with other fluorophores. Rather, this difference is attributed to differing environments experienced by the CY-3 label in the apo- and holo-forms. In some variants (H94C, Alexander, R. S., Kiefer, L. L., Fierke, C. A., Christianson, D. W. (1993) *Biochemistry* 32, 1510–1518; T200C, Krebs, J. F., Fierke, C. A., Alexander, R. S., and Christianson, D. W. (1991) *Biochemistry* 30, 9150–9153; as well as wild type enzyme (Alexander, R. S., Nair, S. K., and Christianson, D. W. (1991) *Biochemistry* 30, 11064–11072) histidine 64 can exhibit dramatically different conformations in an homogenous preparation. Thus a fluorophore coupled to the protein backbone at the same point may also exist in different conformations relative to the rest of the protein depending upon the occupancy of the metal ion binding site. We note that the conformations wild type holo- and apo-enzyme as determined by x-ray crystallography are quite similar.

Figure 11:
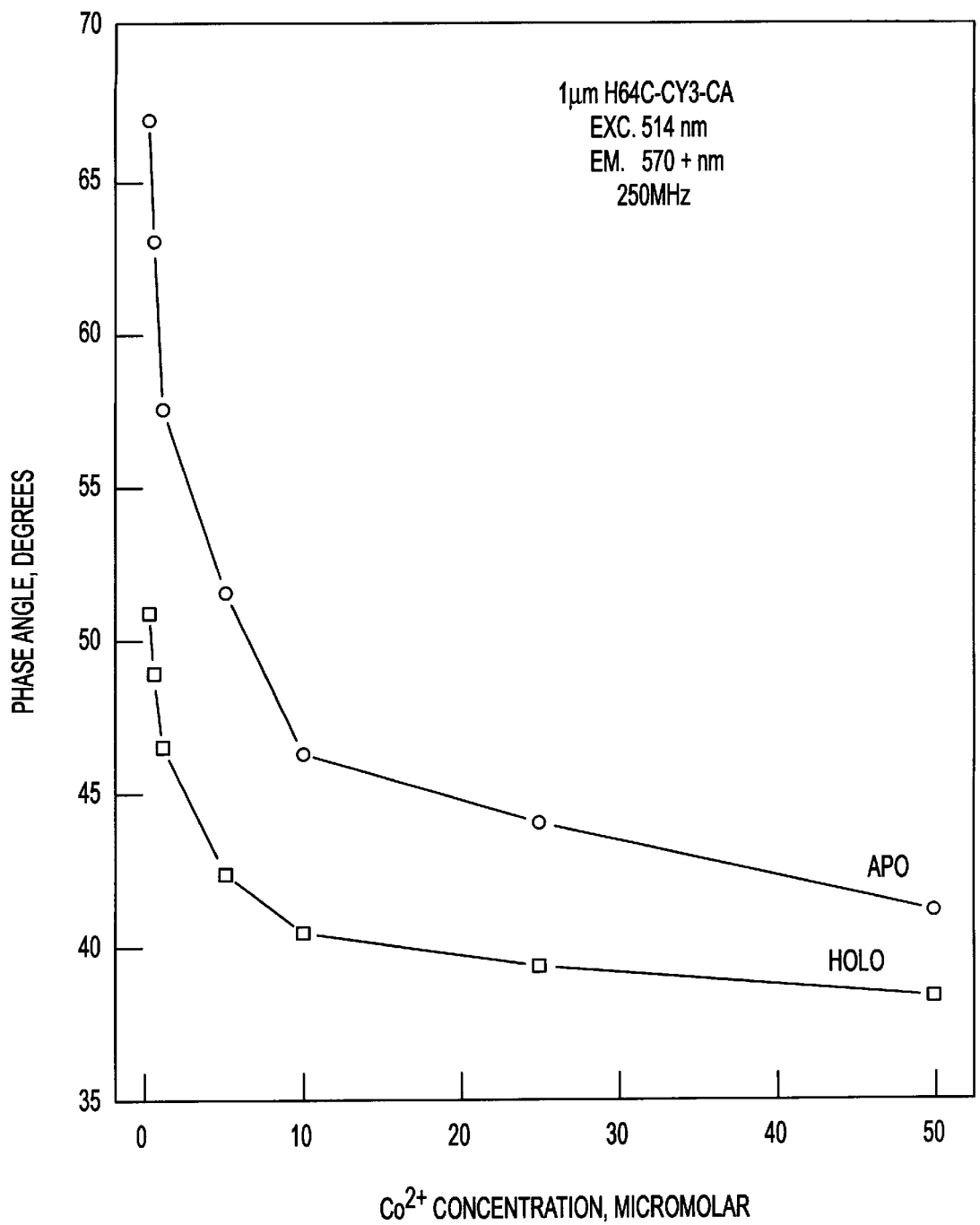
FIG. 11. Phase angles at 250 MHz modulation of 1 uM H64C-CY-3 labeled holo-( ) and apo-(o) carbonic anhydrases in solution as a function of cobalt concentration.

We chose to test this capability for measuring metal ion concentrations through a short length of optical fiber. Thus, we entrapped H64C-CY-3-apoCA in a 5% polyacrylamide gel which could be immobilized on the end of a fiber (Barnard, S. M., and Walt, D. R. (1991) *Nature* 353, 338–340) and measured the time-dependent phase angles at a fixed frequency upon dipping the fiber tip into a solution containing $Co^{2+}$ ion; results are shown for two different metal ion concentrations (FIG. 11). This configuration is thus a fiber optic metal ion biosensor based on fluorescence lifetime measurement. For these experiments we did not use a reference and thus the phase angles are arbitrary; the relevant consideration is the difference in phase angle between the zero time (zero $Co^{2+}$) phase angle and that at the particular time point. The phase angle drift of this particular fluorometer has been measured at less than 0.3 degree per day, and is less than one degree per month. Despite the relatively thick gel layer (0.5 to 1.0 mm), the response to added $Co^{2+}$ was not slow, achieving 90 percent of the final response within a few minutes at both concentrations.

EXAMPLE 6

Figure 15:
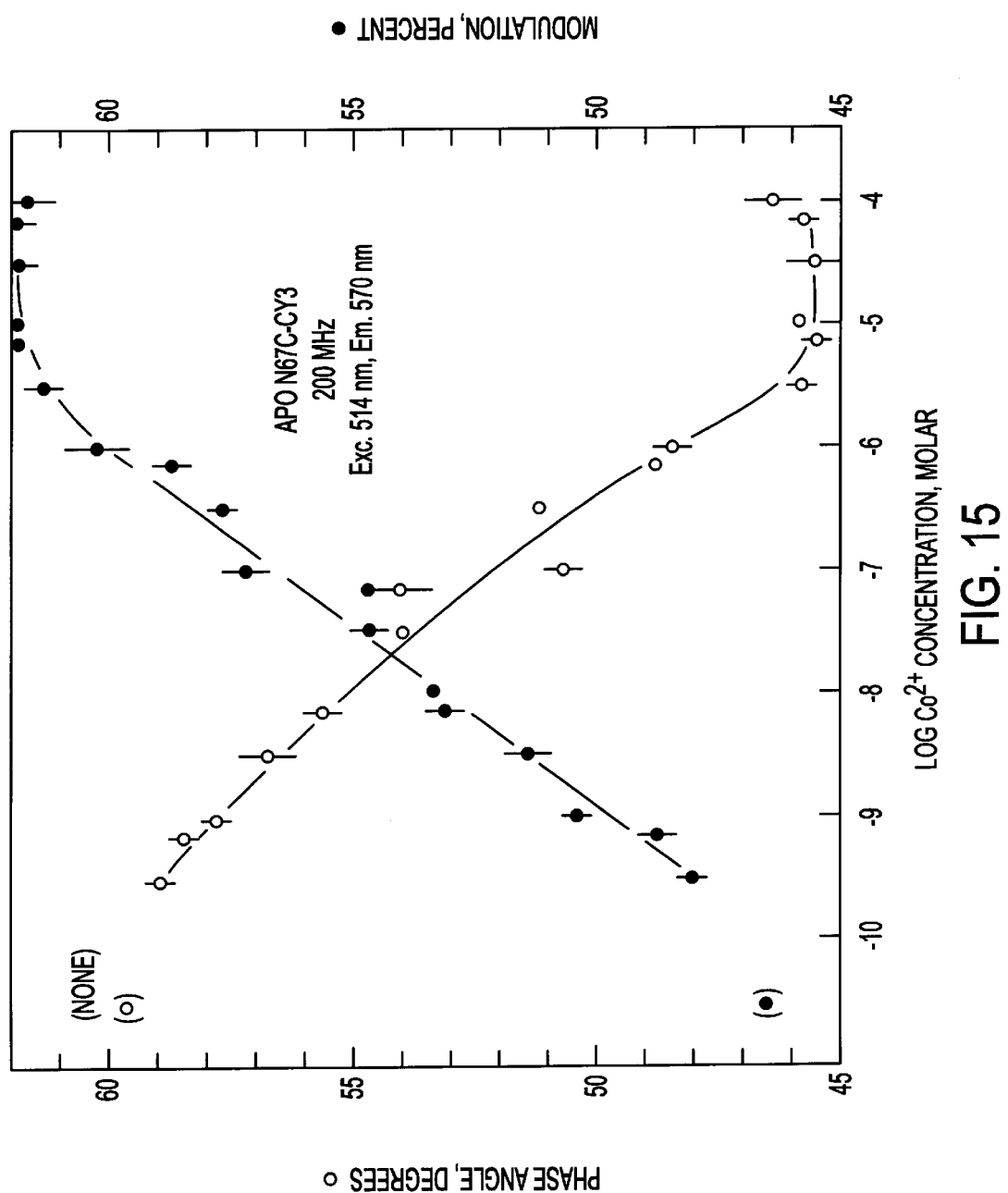
FIG. 15. Frequency-dependent phase angles and demodulations of N67C-CY-3-apocarbonic anhydrase at 200 MHz measured for varying concentrations of $Co^{+2}$.

Site-directed mutants of human carbonic anhydrase II (N67C, H64C) were prepared as previously described (Alexander et al., Biochemistry 32:1510 (1993)). Labeling with CY-3 iodoacetamide at the cysteine residue introduced into the protein (the existing cysteine at position 206 is unreactive) and removal of the active site zinc ion were performed as described previously (Thompson et al., Biosensors & Bioelectronics, 11:6/7 pp. 551–564 (1996)). Co was inserted into the apoprotein active site by addition of excess $CoCl_2$ (see FIG. 15). Absorption spectra were obtained on a Hewlett-Packard HP 8452A spectrophotometer using a solution of human holocarbonic anhydrase II with a closely matched protein concentration as the blank (Alexander et al., Biochemistry 32:1510 (1993)). The spectra obtained were essentially identical to those appearing in the literature. Steady state intensity measurements were obtained on an SLM 8000c and frequency domain fluorescence data were obtained using an ISS K2 phase fluorometer with an Omnichrome air-cooled CW argon ion laser emitting 50 mW at 514 nm for excitation and Rose Bengal in ethanol as reference.

Figure 12:
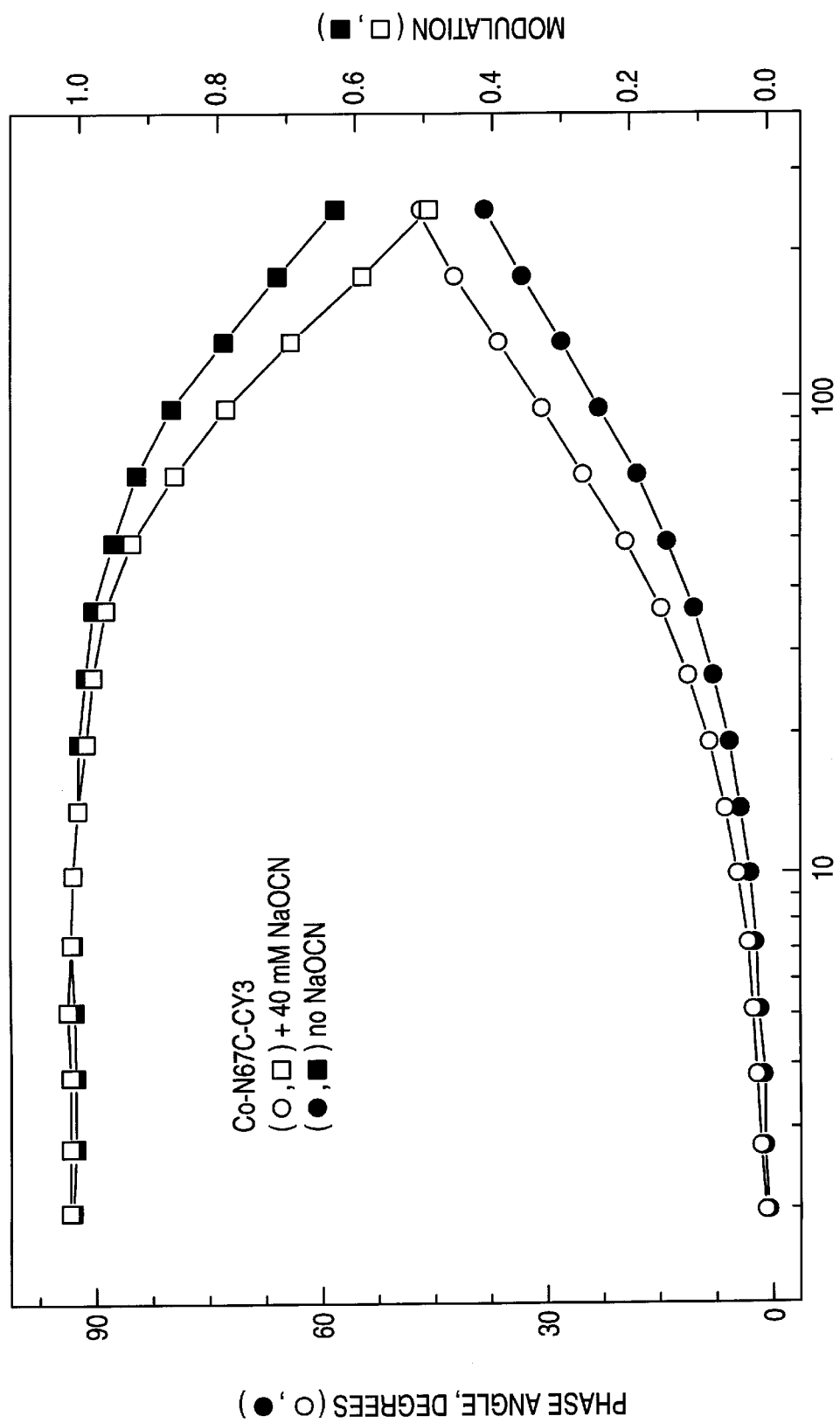
FIG. 12. Fluorescence lifetime-based cyanate determination. Frequency-dependent phases (circles) and modulation (squares) are depicted for Co-N67C-Cy3 in the absence (filled symbols), and presence of 40 mM NaOCN (open symbols) at the same pH.
Figure 13:
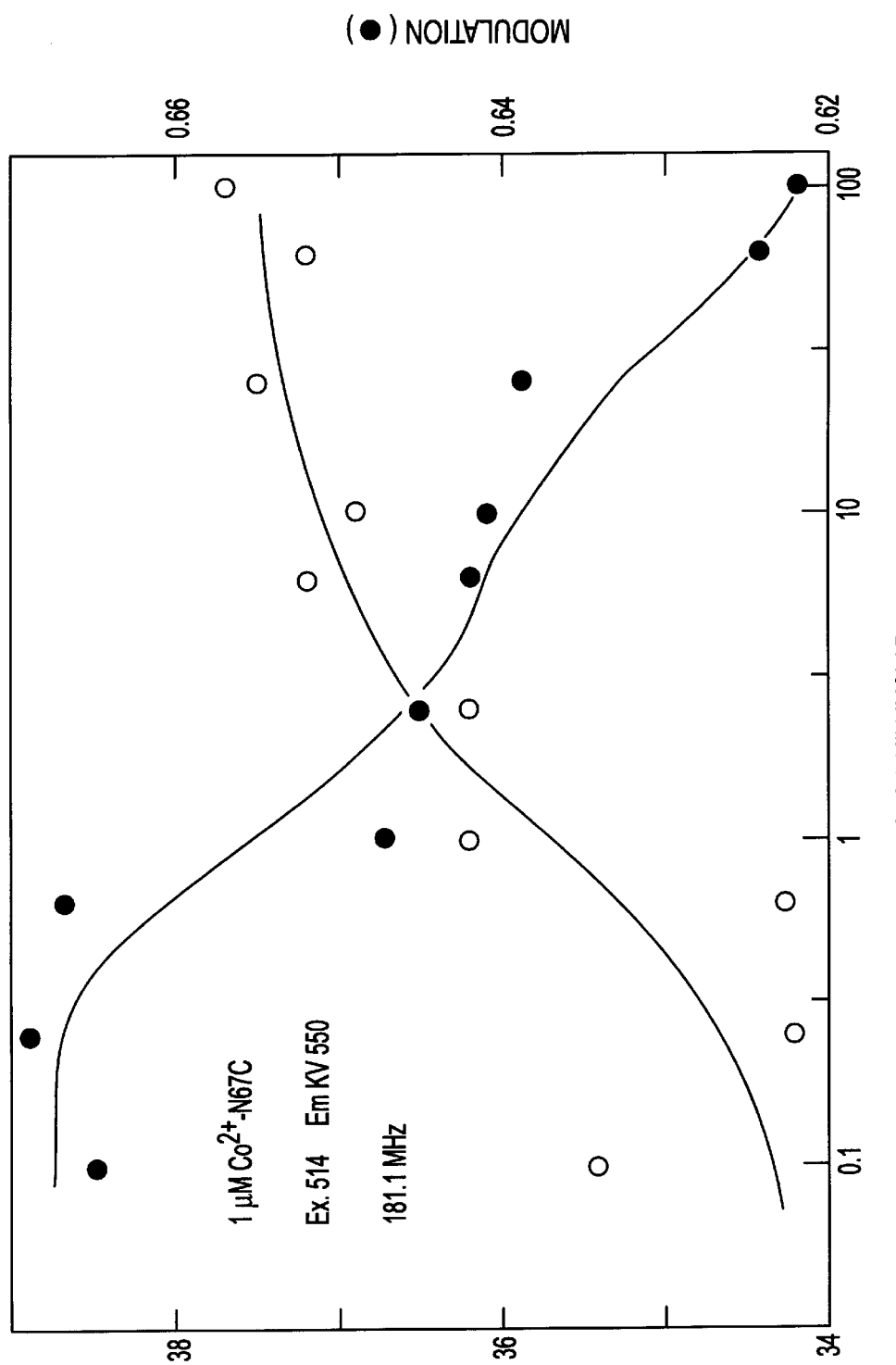
FIG. 13. Fluorescence lifetime-based cyanate determination. Phase (open circles) and modulation (filled circles) of Co-N67C-CY3 are depicted at 181.1 MHz as a function of added cyanate concentration.
Figure 14:
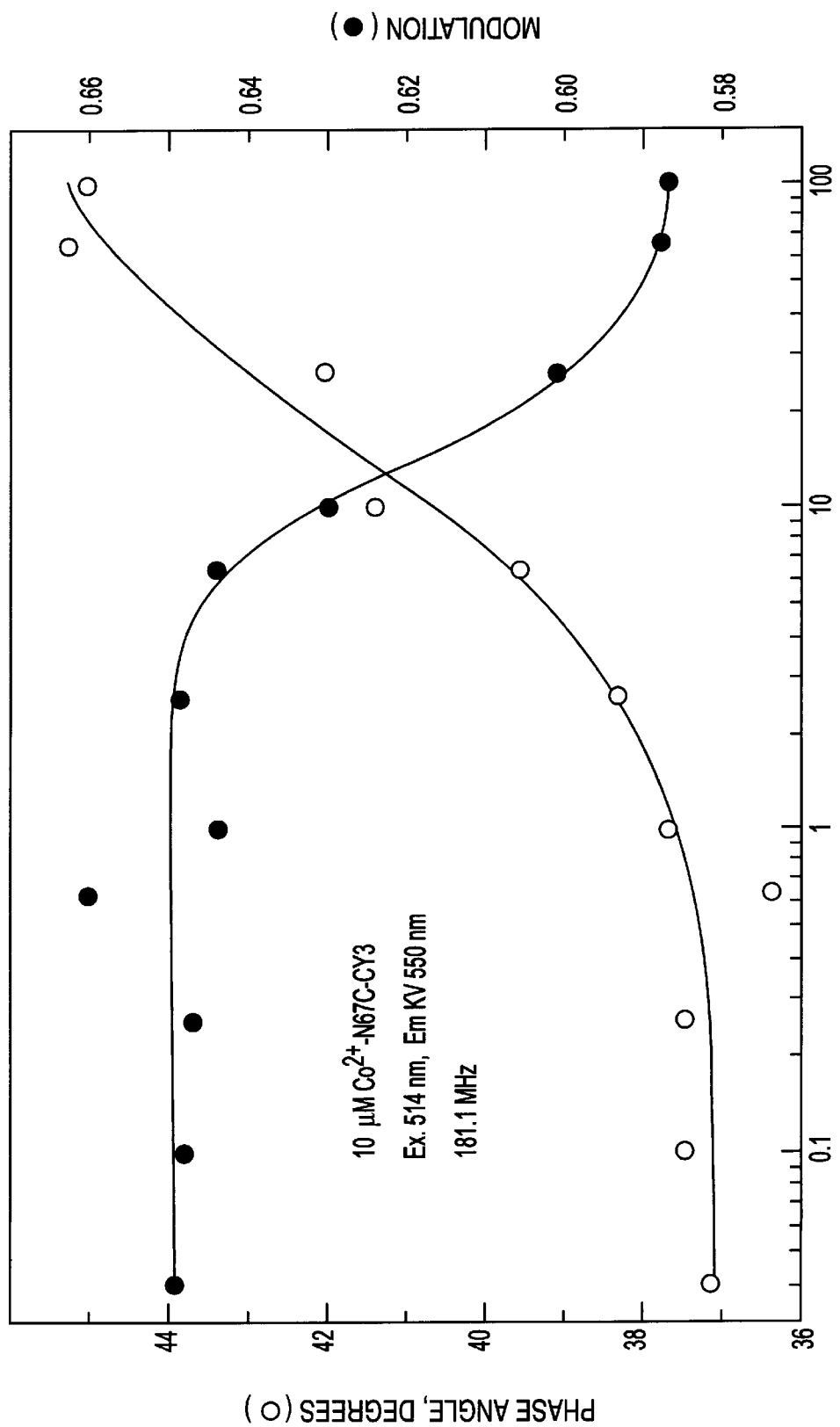
FIG. 14. Fluorescence lifetime-based cyanide determination. Phase (open circles) and modulation (filled circles) of Co-N67C-CY3 are depicted at 181.1 MHz as a function of added cyanide concentration.

We measured the phase angle and demodulation at 181.1 MHz of Co-N67C-CA in the presence of increasing concentrations of both cyanate and cyanide; the results are shown as FIGS. 13 and 14, respectively. In the case of cyanate the differences in time-dependence of the fluorescence in its presence and absence depicted in FIG. 12 are modest, and thus we would expect the phases and modulations to show only a slight change. This is indeed the case, as the phases only change three degrees and the modulation by about four percent. On the other hand, the changes in phase angle and modulation in the presence of cyanide ion are more pronounced, ranging to six degrees and eight percent, respectively. These differences are large enough to be analytically useful, in that the ordinary accuracy and precision of phase and modulation measurements are typically a few tenths of a degree and a few tenths of a percent, respectively. These values are also typical of the standard deviations of our measurements.

All references cited herein are incorporated by reference in their entirety.

While the invention has been described in detail, and with reference to specific embodiments thereof, it will be apparent to one of ordinary skill in the art that various changes and modifications can be made therein without departing from the spirit and scope thereof.

We claim:

1. A method of testing a sample for the presence of an anion comprising the steps of:

reacting a metallo-enzyme attached to a photoluminescent donor label with said sample, said metallo-enzyme being able to reversibly bind said anion, resulting in a metallo-enzyme-anion complex, to quench the photoluminescence, altering the degree of quenching of said photoluminescent donor label in a proximity-dependent quenching process by binding of said anion, measuring the degree of said quenching by determining the change in intensity or lifetime of photoluminescent emission, relating the degree of quenching to the fraction of said metallo-enzyme with bound anion, and to the binding affinity of said metallo-enzyme, thereby determining the presence of said anion wherein the proximity between said donor label and said anion is $r \leq 0.75R_0$, wherein $R_0$ is the Förster distance where energy transfer is fifty percent efficient.

2. The method of claim 1, wherein the presence of said anion is determined by measuring the concentration of the anion.

3. The method of claim 1, wherein said anion is selected from the group consisting of $OH^-$, $CN^-$, $CNO^-$, $NO_3^-$, $CH_3COO^-$, $HCOO^-$, $HCO_3^-$, $C_6H_5O^-$, $N_3^-$, $C_6H_3O_5N_2^-$, $SCN^-$, $HS^-$.

4. A method of testing a sample for the presence of a metal ion comprising the steps of:

reacting an enzyme attached to a photoluminescent donor label with said sample in the presence of a colored ligand wherein said colored ligand is selected from the group consisting of azosulfamide, 4-(4, dimethylaminophenyl) azophenyl sulfonamide and salicylazobenzenesulfonamide, creating a metallo-enzyme, wherein the presence of said metal ion in a binding site of the enzyme permits the colored ligand to bind, thereby bringing it into closer proximity to said photoluminescent donor label, altering the degree of quenching of said photoluminescent donor label in a proximity-dependent quenching process by binding of said metal ion, measuring the degree of quenching by determining the change in intensity or lifetime of photoluminescent emission, relating the degree of quenching to the fraction of said metallo-enzyme with bound metal ion, and to the binding affinity of said metallo-enzyme, thereby determining the presence of said metal ion wherein the proximity between said donor label and said metal ion is $r \leq 0.75R_0$, wherein $R_0$ is the Förster distance where energy transfer is fifty percent efficient.

5. The method of claim 4, wherein said colored ligand is azosulfamide.

6. The method of claim 4, wherein the presence of said metal ion in said sample is determined by measuring the concentration of said metal ion.

7. The method of claim 6, wherein said enzyme is selected from the group consisting of carbonic anhydrase, alkaline phosphatase, leucine aminopeptidase, carboxypeptidase, laccase, azurin and urease.

8. The method of claim 7 wherein said enzyme is a mutant enzyme.

* * * * *